United States Patent
Lee et al.

(10) Patent No.: US 11,135,161 B2
(45) Date of Patent: Oct. 5, 2021

(54) INTRAVESICAL DEVICE FOR CONTROLLED DRUG DELIVERY

(71) Applicant: TARIS Biomedical LLC, Lexington, MA (US)

(72) Inventors: Heejin Lee, Bedford, MA (US); Michael J. Cima, Winchester, MA (US); Karen Daniel, Newton, MA (US); Cheryl Larrivee-Elkins, Framingham, MA (US)

(73) Assignee: TARIS BIOMEDICAL LLP, Lexington, MA (US)

( * ) Notice: Subject to any disclaimer, the term of this patent is extended or adjusted under 35 U.S.C. 154(b) by 393 days.

(21) Appl. No.: 15/815,843

(22) Filed: Nov. 17, 2017

(65) Prior Publication Data
US 2018/0071213 A1    Mar. 15, 2018

Related U.S. Application Data

(60) Continuation of application No. 14/677,182, filed on Apr. 2, 2015, now abandoned, which is a division of
(Continued)

(51) Int. Cl.
  *A61K 9/00* (2006.01)
  *A61K 31/167* (2006.01)
  *A61M 31/00* (2006.01)

(52) U.S. Cl.
  CPC .......... *A61K 9/0092* (2013.01); *A61K 9/0004* (2013.01); *A61K 9/0034* (2013.01); *A61K 31/167* (2013.01); *A61M 31/002* (2013.01)

(58) Field of Classification Search
  CPC .. A61K 9/0092; A61K 9/0004; A61K 31/167; A61K 9/0034; A61M 31/002
  See application file for complete search history.

(56) References Cited

U.S. PATENT DOCUMENTS 3,089,815 A  *  5/1963  Kupelwieser ........ A61K 9/0019
                                              514/774
3,854,480 A     12/1974  Zaffaroni
(Continued)

FOREIGN PATENT DOCUMENTS

DE     3332156 A1    3/1985
EP     0572932 A2    12/1993
(Continued)

OTHER PUBLICATIONS

Welk et al., "Dyspareunia Response in Patients with Interstitial Cystitis Treated with Intravesical Lidocaine, Bicarbonate, and Heparin," Urology, vol. 71, No. 1 (2008), 67-70, Elsevier Inc.
(Continued)

*Primary Examiner* — Bradley J Osinski
(74) *Attorney, Agent, or Firm* — Eversheds Sutherland (US) LLP

(57) ABSTRACT

Implantable devices and methods for delivery of lidocaine or other drugs to a patient are provided. In one embodiment, the device includes a first drug portion which has a first drug housing which contains a first drug formulation in a solid form which includes a pharmaceutically acceptable salt of lidocaine; and a second drug portion which includes a second drug housing which contains a second drug formulation which includes lidocaine base. In another embodiment, the device includes a drug reservoir component which has an elastic tube having at least one lumen bounded by a porous sidewall having an open-cell structure, a closed-cell structure, or a combination thereof; and a drug formulation contained within the at least one lumen, wherein the device is deformable between a low-profile deployment shape and a relatively expanded retention shape.

13 Claims, 9 Drawing Sheets

Related U.S. Application Data application No. 12/851,494, filed on Aug. 5, 2010, now Pat. No. 9,017,312, which is a continuation-in-part of application No. 12/825,215, filed on Jun. 28, 2010.

(60) Provisional application No. 61/241,277, filed on Sep. 10, 2009.

(56) References Cited

U.S. PATENT DOCUMENTS

| | | | |
|---|---|---|---|
| 3,888,975 A | 6/1975 | Ramwell | |
| 3,901,232 A | 8/1975 | Michaels et al. | |
| 3,935,860 A | 2/1976 | Hoff | |
| 3,948,254 A * | 4/1976 | Zaffaroni | A61K 9/0004 |
| | | | 128/833 |
| 4,016,251 A | 4/1977 | Higuchi et al. | |
| 4,235,236 A | 11/1980 | Theeuwes | |
| 4,326,522 A | 4/1982 | Guerrero et al. | |
| 4,392,848 A | 7/1983 | Lucas et al. | |
| 4,449,980 A | 5/1984 | Millar et al. | |
| 4,475,916 A | 10/1984 | Himmelstein | |
| 4,578,075 A | 3/1986 | Urquhart et al. | |
| 4,578,263 A | 3/1986 | Whitehead | |
| 4,587,075 A * | 5/1986 | Butcher | B29B 13/024 |
| | | | 264/150 |
| 4,629,449 A | 12/1986 | Wong | |
| 4,655,219 A | 4/1987 | Petruzzi | |
| 4,678,463 A | 7/1987 | Millar | |
| 4,681,583 A * | 7/1987 | Urquhart | A61J 3/07 |
| | | | 424/453 |
| 4,731,054 A | 3/1988 | Billeter et al. | |
| 4,871,542 A | 10/1989 | Vilhardt | |
| 4,968,507 A | 11/1990 | Zentner et al. | |
| 4,973,304 A | 11/1990 | Graham et al. | |
| 5,366,738 A | 11/1994 | Rork et al. | |
| 5,441,550 A | 8/1995 | Hassenboehler, Jr. et al. | |
| 5,499,997 A | 3/1996 | Sharpe et al. | |
| 5,516,522 A | 5/1996 | Peyman et al. | |
| 5,551,954 A | 9/1996 | Buscemi et al. | |
| 5,709,874 A | 1/1998 | Hanson et al. | |
| 5,788,980 A | 8/1998 | Nabahi | |
| 5,795,591 A | 8/1998 | Lee et al. | |
| 5,797,898 A | 8/1998 | Santini, Jr. et al. | |
| 5,830,230 A | 11/1998 | Berryman et al. | |
| 5,851,217 A | 12/1998 | Wolff et al. | |
| 5,855,906 A | 1/1999 | McClay | |
| 5,869,081 A | 2/1999 | Jackanicz et al. | |
| 5,972,372 A | 10/1999 | Saleh et al. | |
| 5,989,581 A | 11/1999 | Groenewegen | |
| 6,039,967 A | 3/2000 | Ottoboni et al. | |
| 6,039,968 A | 3/2000 | Nabahi | |
| 6,083,933 A | 7/2000 | Hahn | |
| 6,086,909 A | 7/2000 | Harrison et al. | |
| 6,139,535 A | 10/2000 | Greelis et al. | |
| 6,159,143 A | 12/2000 | Lennox | |
| 6,168,801 B1 | 1/2001 | Heil, Jr. et al. | |
| 6,171,298 B1 * | 1/2001 | Matsuura | A61L 17/145 |
| | | | 604/891.1 |
| 6,183,461 B1 | 2/2001 | Matsuura et al. | |
| 6,207,180 B1 | 3/2001 | Ottoboni et al. | |
| 6,293,923 B1 | 9/2001 | Yachia et al. | |
| 6,398,718 B1 | 6/2002 | Yachia et al. | |
| 6,416,780 B1 | 7/2002 | Passmore et al. | |
| 6,444,224 B1 | 9/2002 | Rathbone et al. | |
| 6,464,999 B1 | 10/2002 | Huo et al. | |
| 6,482,837 B1 | 11/2002 | Wood | |
| 6,491,666 B1 | 12/2002 | Santini, Jr. et al. | |
| 6,524,608 B2 | 2/2003 | Ottoboni et al. | |
| 6,682,473 B1 | 1/2004 | Matsuura et al. | |
| 6,712,784 B2 | 3/2004 | Huang | |
| 6,730,072 B2 | 5/2004 | Shawgo et al. | |
| 6,746,421 B2 | 6/2004 | Yachia et al. | |
| 6,749,617 B1 | 6/2004 | Palasis et al. | |
| 6,753,011 B2 | 6/2004 | Faour | |
| 6,808,522 B2 | 10/2004 | Richards et al. | |
| 6,875,208 B2 | 4/2005 | Santini, Jr. et al. | |
| 6,899,890 B2 | 5/2005 | Kirschner et al. | |
| 6,932,810 B2 | 8/2005 | Ryan | |
| 6,951,654 B2 | 10/2005 | Malcom et al. | |
| 6,973,718 B2 | 12/2005 | Sheppard, Jr. et al. | |
| 6,976,950 B2 | 12/2005 | Connors et al. | |
| 6,976,951 B2 | 12/2005 | Connors et al. | |
| 6,988,983 B2 | 1/2006 | Connors et al. | |
| 7,005,138 B2 | 2/2006 | Mahashabde et al. | |
| 7,074,178 B2 | 7/2006 | Connors et al. | |
| 7,232,421 B1 | 6/2007 | Gambale et al. | |
| 7,521,064 B2 | 4/2009 | Saxena et al. | |
| 7,647,112 B2 | 1/2010 | Tracey et al. | |
| 2003/0059456 A1 | 3/2003 | Malcom et al. | |
| 2003/0118649 A1 | 6/2003 | Gao et al. | |
| 2003/0118692 A1 | 6/2003 | Wang et al. | |
| 2003/0139800 A1 | 7/2003 | Campbell | |
| 2003/0229263 A1 | 12/2003 | Connors et al. | |
| 2004/0022824 A1 | 2/2004 | Li et al. | |
| 2004/0034332 A1 | 2/2004 | Uhland | |
| 2004/0149294 A1 | 8/2004 | Gianchandani et al. | |
| 2004/0220552 A1 | 11/2004 | Heruth et al. | |
| 2004/0260272 A1 | 12/2004 | Friedman et al. | |
| 2005/0228482 A1 | 10/2005 | Herzog et al. | |
| 2005/0234013 A1 | 10/2005 | Parsons | |
| 2005/0234431 A1 | 10/2005 | Williams et al. | |
| 2005/0238733 A1 | 10/2005 | Henry | |
| 2006/0105010 A1 | 5/2006 | Rahe et al. | |
| 2006/0122689 A1 | 6/2006 | Kocur et al. | |
| 2006/0234978 A1 | 10/2006 | Marcum | |
| 2006/0259118 A1 | 11/2006 | Pal et al. | |
| 2006/0264897 A1 | 11/2006 | Lobl et al. | |
| 2006/0264912 A1 | 11/2006 | McIntyre et al. | |
| 2007/0172507 A1 | 7/2007 | Zupkas et al. | |
| 2007/0172508 A1 | 7/2007 | Zupkas et al. | |
| 2007/0202151 A1 * | 8/2007 | Lee | A61K 9/0034 |
| | | | 424/426 |
| 2007/0254014 A1 | 11/2007 | Ahmed et al. | |
| 2008/0051740 A1 | 2/2008 | Sokal et al. | |
| 2009/0004246 A1 | 1/2009 | Woolfson et al. | |
| 2009/0149833 A1 * | 6/2009 | Cima | A61M 25/0102 |
| | | | 604/517 |
| 2009/0317465 A1 | 12/2009 | Peppas | |
| 2010/0003297 A1 | 1/2010 | Tobias et al. | |
| 2010/0076261 A1 | 3/2010 | Neeman et al. | |
| 2010/0152704 A1 | 6/2010 | Lee et al. | |
| 2010/0330149 A1 | 12/2010 | Daniel et al. | |
| 2010/0331770 A1 | 12/2010 | Lee et al. | |
| 2011/0152839 A1 | 6/2011 | Cima et al. | |
| 2013/0129824 A1 | 5/2013 | Daniel et al. | |
| 2014/0221981 A1 | 8/2014 | Cima et al. | |
| 2014/0350473 A1 | 11/2014 | Lee et al. | |

FOREIGN PATENT DOCUMENTS

| | | |
|---|---|---|
| WO | 1997/044021 A1 | 11/1997 |
| WO | 1998/031415 A1 | 7/1998 |
| WO | 1999/018884 A1 | 4/1999 |
| WO | 2000/040234 A1 | 7/2000 |
| WO | 2001/067991 A1 | 9/2001 |
| WO | 2002/000203 A1 | 1/2002 |
| WO | 2002/005800 A2 | 1/2002 |
| WO | 2002/085428 A2 | 10/2002 |
| WO | 2003/009882 A2 | 2/2003 |
| WO | 2004/037318 A2 | 5/2004 |
| WO | 2005/072751 A1 | 8/2005 |
| WO | 2005/115245 A1 | 12/2005 |
| WO | 2006/121969 A1 | 11/2006 |
| WO | 2007/021964 A2 | 2/2007 |
| WO | 2007/115259 A2 | 10/2007 |
| WO | 2008/038281 A2 | 4/2008 |
| WO | 2008/051889 A1 | 5/2008 |
| WO | 2008/115536 A2 | 9/2008 |
| WO | 2009/029958 A2 | 3/2009 |
| WO | 2009/076547 A2 | 6/2009 |
| WO | 2010/019507 A2 | 2/2010 |

(56) References Cited

FOREIGN PATENT DOCUMENTS

OTHER PUBLICATIONS

Woolfson, et al., "Design of a silicone reservoir intravaginal ring for the delivery of oxybutynin," Journal of controlled Release, vol. 91 (2003), pp. 465-476, Elsevier B.V.

Woolfson, et al., "Design of an intravaginal ring for the controlled delivery of 17JI-estradiol as its 3-acetate ester," Journal of Controlled Release, vol. 61 (1999), pp. 319-328, Elsevier Science B.V.

Wright, et al., Pumps/Osmotic, Encyclopedia of Controlled Drug Delivery, vol. 2 (1999), pp. 896-920, New York; John Wiley.

Wright, et al., "DUROS® Osmotic Pharmaceutical Systems for Parenteral & Site-Directed Therapy,", Drug Delivery Technologies: Implantable Technology, vol. 3, No. 1, 2003, pp. 1-15 (http://www.drugdeliverytech.com/cgi-bin/articles.cgi?idArticle=115).

Estebe, et al., "Alkalinization of Intracuff Lidocaine Improves Endotracheal Tube-Induced Emergence Phenomena," Anesth Analg, vol. 94 (2002), pp. 227-230, International Anesthesia Research Society.

Ali, et al., "Lidocaine as Endotracheal Tube Cuff Inflating Agent," JAFMC Bangladesh, vol. 5, No. 1 (Jun. 2009), pp. 25-28.

Amark, et al., "Follow-Up of Long-Time Treatment with Intravesical Oxybutynin for Neurogenic Bladder in Children," European Urology, vol. 34 (1998), pp. 148-153.

Au, et al., "Methods to Improve Efficacy of Intravesical Mitomycin C: Results of a Randomized Phase III Trial," Journal of the National Cancer Institute, vol. 93, No. 8 (Apr. 18, 2001).

Bade, et al., "A Placebo-Controlled Study of Intravesical Pentosanpolysulphate for the Treatment of Interstitial Cystitis," British Journal of Urology, vol. 79 (1997), pp. 168-171.

Beiko, et al., "Urinary Tract Biomaterials," The Journal of Urology, vol. 171 (Jun. 2004), pp. 2438-2444.

Birch, et al., "Absorption Characteristics of Lignocaine Following Intravesical Instillation," Scand J Urol Nephrol, vol. 28 (1994), pp. 359-364.

Burmeister, et al., Intravesical instillation of trospium chloride, oxybutynin and verapamil for relaxation of the bladder detrusor muscle. A placebo controlled, randomized clinical test, Arzneimittelforschung, vol. 48, No. 5 (May 1998); pp. 486-491. Abstract.

Carr, et al., "Evaluation of a transoral delivery system for topical anesthesia," J Am Dent Assoc, vol. 132 (2001), pp. 1714-1719.

Clemens, et al, "Interstitial Cystitis and Painful Bladder Syndrome," Urological Diseases in America, (2007), pp. 125-154.

Collins, et al., "How Common is Prostatitis? A National Survey of Physician Visits," The Journal of Urology, vol. 159 (Apr. 1998), pp. 1224-1228.

Curhan, et al., "Epidemiology of Interstitial Cystitis: A Population Based Study," The Journal of Urology, vol. 161 (Feb. 1999), pp. 549-552.

Dentipatch (lidocaine) Patch [Noven Pharmaceuticals, Inc.], downloaded from http://dailymed.nlm.nih.gov/dailymed/fdaDrugXsl.cfm?id=1543&type=display on Feb. 22, 2007.

Dollo, et al., "Endotracheal tube cuffs filled with lidocaine as a drug delivery system: in vitro and in vivo Investigations," European Journal of Pharmaceutical Sciences, vol. 13 (2001), pp. 319-323, Elsevier Sciences B.V.

Erickson, et al., "Interstitial Cystitis," Int Urogynecol J, vol. 9 (1998), pp. 174-183, Springer-Verlag London Ltd.

Estebe, et al., "Alkalinization of intra-cuff lidocaine and use of gel lubrication protect against tracheal tube-induced emergence phenomena," British Journal of Anesthesia, vol. 92, No. 3 (2004), pp. 361-366, The Board of Management and Trustees of the British Journal of Anesthesia.

Estebe, et al., "Alkalinization of Intracuff Lidocaine: Efficacy and Safety," Anesth Analg, vol. 101 (2005), pp. 1536-1541, International Anesthesia Research Society.

Fraser, et al., "The Future of Bladder Control—Intravesical Drug Delivery, a Pinch of Pepper, and Gene Therapy," Reviews in Urology, vol. 4, No. 1 (2002).

Gammaitoni, et al., "Safety and Tolerability of the Lidocaine Patch 5%, a Targeted Peripheral Analgesic: A Review of the Literature," J Clin Pharmacol, vol. 43 (2003), pp. 111-117, American College of Clinical Pharmacology.

Gasión, et al., "Improving Efficacy of Intravesical Chemotherapy," European Urology, vol. 50 (2006), pp. 225-234, Elsevier B.V.

Giannantoni, et al., "New Frontiers in Intravesical Therapies and Drug Delivery," European Urology, vol. 50 (2006), pp. 1183-1193, Elsevier B.V.

Grayson, et al., Molecular release from a polymeric micro reservoir device: Influence of chemistry, polymer swelling, and loading on device performance, J. Biomed Mat Res, vol. 69A, No. 3 (2004), pp. 502-512.

Grayson, et al. "Multi-pulse drug delivery from a resorbable polymeric microchip device," Nature Publishing Group, (2003), pp. 1-6.

Henry, et al., "Absorption of Alkalized Intravesical Lidocaine in Normal and Inflamed Bladders: A Simple Method for Improving Bladder Anesthesia," The Journal of Urology, vol. 165 (Jun. 2001) pp. 1900-1903, American Urological Association, Inc., U.S.A.

Henry, et al., "Alkalinized Intravesical Lidocaine to Treat Interstitial Cystitis: Absorption Kinetics in Normal and Interstitial Cystitis Bladders," Urology, vol. 57, Supplement 6A (Jun. 2001), p. 119.

Henry, et al., "Topical Anesthesia of the Bladder" Abstracts—Tuesday, Jun. 22 (AM)—Poster Discussion Session VI—Obstetrics/Regional, 1999, p. A61B, vol. 46, No. 5, Canadian Journal of Anesthesia—Journal Canadien d'Anesthesie.

Highley, et al., "Intravesical Drug Delivery Pharmacokinetic and Clinical Considerations," Clinical Pharmacokinetic, vol. 37, No. 1 (Jul. 1999), pp. 59-73, Adis International Limited.

Interstitial Cystitis Network: Patient Handbook: Treatments; Bladder Instillations (http:///www.ic-network.com/handbook/instill.html) last updated Mar. 16, 2006.

International Search Report and Written Opinion for PCT/US2010/048266, dated Feb. 15, 2012.

Jiranantarat, et al., "Analgesic Effect of Intraperitoneal Instillation of Bupivacaine for Postoperative Laparoscopic Cholecystectomy," J Med Assoc Thai, vol. 85, Suppl. 3 (Sep. 2002), pp. S897-S903.

Kim, et al., "Antimuscarinic Agents Exhibit Local Inhibitory Effects on Muscarinic Receptors in Bladder-Afferent Pathways," Urology, vol. 65, No. 2 (2005), pp. 238-242, Elsevier Inc.

Larsson, et al., "Effect of Intraperitoneal Instillation of 32% Dextran 70 on Postoperative Adhesion Formation After Tubal Surgery," Acta Obstet Gynecol Scand, vol. 64 (1985), pp. 437-441.

Li, et al. "Water Based Silicone Elastomer Controlled Release Tablet Film Coating III—Drug Release Mechanisms," Drug Development and Industrial Pharmacy, vol. 15, No. 12 (1989), pp. 1943-1968, Marcel Dekker, Inc.

Malmstrom, Per-Uno, "Intravesical therapy of superficial bladder cancer," Critical Reviews in Oncology Hematology, vol. 47 (2003), pp. 109-126, Elsevier Science.

Morimoto, et al., "Management of Patients with Recurrent Nephrosis and Intractable Edema by Intraperitoneal Instillation of Icodextrin Solution," Peritoneal Dialysis International, vol. 28, No. 5 (Sep. 2008), pp. 559-561.

Parsons, et al., "Bladder Surface Glycosaminoglycans: An Epithelial Permeability Barrier," The Journal of Urology, vol. 143, No. 1 (1990), pp. 139-142.

Parsons, C. Lowell, "Successful Downregulation of Bladder Sensory Nerves with Combination of Heparin and Alkalinized Lidocaine in Patients with Interstitial Cystitis," Urology, vol. 65, No. 1 (2005), pp. 45-48.

Russell, et al., "High-performance liquid chromatographic determination of 17β-estradiol and 17β-estradiol-3-acetate solubilities and diffusion coefficients in silicone elastomeric intravaginal rings," Journal of Chromatography B, vol. 744 (2000), pp. 157-163, Elsevier Science B.V.

Saitoh, et al., "Effects of Intravesical Instillation of Resiniferatoxin on Bladder Function and Nociceptive Behavior in Freely Moving, Conscious Rats," The Journal of Urology, vol. 179 (Jan. 2008), pp. 359-364, American Urological Association, U.S.A.

Santus, et al., "Osmotic drug delivery: a review of the patent literature," Journal of Controlled Release, vol. 35 (1995), pp. 1-21.

(56) References Cited

OTHER PUBLICATIONS

Sconzo, et al., "In Vitro Diffusion of Lidocaine across Endotracheal Tube Cuffs," Regional Anesthesia, (Jan.-Feb. 1990), pp. 37-40.
Spratt, et al., "Clinical Delivery System for Intraperitoneal Hyperthermic Chemotherapy," Cancer Research, vol. 40 (Feb. 1980), pp. 256-260.
Stymne, et al., "Plasma concentrations of lignocaine and prilocaine after a 24-h application of analgesic cream (emla®) to leg ulcers," British Journal of Dermatology, vol. 145 (2001), pp. 530-534, British Association of Dermatologists.
Theeuwes, Felix, "Elementary Osmotic Pump," Journal of Pharm Sci, vol. 64, No. 12 (Dec. 1975), pp. 1987-1991.
Theoharides, et al., "Painful Bladder Syndrome/Interstitial Cystitis: Current Concepts and Role of Nutraceuticals," Seminars in Preventive and Alternative Medicine, vol. 2 (2006), pp. 6-14, Elsevier Inc.
Thombre, et al., "Mechanism of Water Transport in Controlled Porosity Osmotic Devices," Journal of Membrane Science, vol. 40 (1989), pp. 279-310, Elsevier Science Publishers B.V.
Tyagi, et al., "Local Drug Delivery to Bladder Using Technology Innovations," Urological Clinics of North America, vol. 33 (2006), pp. 519-530, Elsevier Inc.
Vassileva, et al., "Novel biocompatible intraperitoneal drug delivery system increases tolerability and therapeutic efficacy of paclitaxel in a human ovarian cancer xenograft model," Cancer Chemother Pharmacol, vol. 60 (2007), pp. 907-914, Springer-Verlag.
Verma, et al., "Formulation aspects in the development of osmotically controlled oral drug delivery systems," Journal of Controlled Release, vol. 79 (2002), pp. 7-27, Elsevier Science B.V.
Walker, et al., "Intravesical Chemotherapy: In Vitro Studies on the Relationship Between Dose and Cytotoxicity," Urological Research, vol. 14 (1986), pp. 137-140, Springer-Verlag.
Walter, et al., "Bioavailability of Trospium Chloride After Intravesical Instillation in Patients with Neurogenic Lower Urinary Tract Dysfunction: A Pilot Study," Neurourology and Urodynamics, vol. 18 (1999), pp. 447-453, Wiley-Liss, Inc.

* cited by examiner

INTRAVESICAL DEVICE FOR CONTROLLED DRUG DELIVERY

CROSS-REFERENCE TO RELATED APPLICATIONS

This application is a continuation of U.S. application Ser. No. 14/677,182, filed Apr. 2, 2015, which is a divisional of U.S. application Ser. No. 12/851,494, Aug. 5, 2010, which is a continuation-in-part of U.S. application Ser. No. 12/825,215 filed Jun. 28, 2010, and which claims the benefit of U.S. Provisional Application No. 61/241,277, filed Sep. 10, 2009. These prior applications are incorporated herein by reference in their entirety.

BACKGROUND

This disclosure relates to controlled drug delivery, particularly implantable devices that can be deployed within the bladder or another site in a patient for controlled drug release.

U.S. Patent Application Publications No. 2007/0202151 and No. 2009/0149833 describe drug delivery devices for minimally invasive deployment and retention in a cavity or lumen in a patient, such as the bladder. The devices resist excretion, such as in response to the forces associated with urination. For example, the devices may include a retention frame, which may be configured into a relatively low profile for deployment into the body, and once implanted may assume a relatively expanded profile to facilitate retention. The devices may provide controlled release of drug over an extended period in a predefined manner. In some embodiments, the devices include a water-permeable silicone tube that defines a drug reservoir for housing a drug and at least one aperture for releasing the drug. The drug may be a highly water soluble drug, such as lidocaine hydrochloride in solid form, and the in vivo drug release mechanism may be partially or predominantly an osmotic pumping mechanism. It would be desirable to provide additional techniques, structures, and/or formulations to enhance control of drug release kinetics in vivo, for example from a device deployed in the bladder.

SUMMARY

Implantable devices and methods for delivery of lidocaine or other drugs to a patient are provided.

In one aspect, the device includes a first drug portion which has a first drug housing which contains a first drug formulation in a solid form which includes a pharmaceutically acceptable salt of lidocaine; and a second drug portion which includes a second drug housing which contains a second drug formulation which includes lidocaine base.

In another aspect, an implantable drug delivery device is provided that includes a drug reservoir component which has an elastic tube having at least one lumen bounded by a porous sidewall having an open-cell structure, a closed-cell structure, or a combination thereof; and a drug formulation contained within the at least one lumen, wherein the device is deformable between a low-profile deployment shape and a relatively expanded retention shape.

In still another aspect, an implantable medical device is provided for controlled drug delivery device that includes (i) a first drug portion that comprises a first drug housing loaded with a first drug formulation comprising a first drug, wherein the first drug housing comprises a first wall that is permeable to water but is substantially impermeable to the first drug and has at least one passageway through the first wall, the first drug portion releasing the first drug in vivo according to a first release profile; and (ii) a second drug portion that comprises a second drug housing loaded with a second drug formulation comprising a second drug, wherein the second drug housing comprises a second wall that is permeable to water and to the second drug, the second drug portion releasing the second drug in vivo according to a second release profile, the second release profile differing from the first release profile; and (iii) a retention portion operably associated with both the first and second drug portions.

In a further aspect, a method is provided for delivering lidocaine into a patient's bladder. In one embodiment, the method includes deploying into the patient's bladder a device which comprises a water permeable housing which contains lidocaine base in solid form; and, following solubilization of the lidocaine base in vivo, releasing from the device the solubilized lidocaine into the bladder through the water permeable housing.

DETAILED DESCRIPTION

Figure 1:
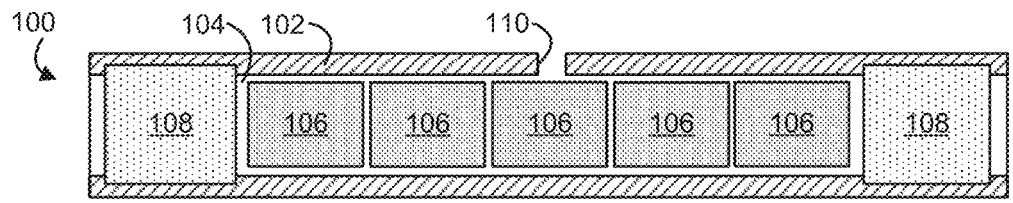
FIG. 1 is a cross-sectional plan view of an embodiment of a drug portion of a drug delivery device, the drug portion configured for osmotically driven drug release.

Described below are implantable devices that can be implanted in a body cavity or lumen for the purpose of delivering drug locally or regionally about an implantation site. For the purposes of the present disclosure, the term "implantation site" generally refers to a site within the body of a human patient or other animal. The implantation site can be any genitourinary site, such as the bladder, urethra, ureters, kidneys, prostate, seminal vesicles, ejaculatory duct, vas deferens, vagina, uterus, fallopian tubes, ovaries or any other location within a urological or reproductive system of the body, among other locations. In particular embodiments, the implantation site is the bladder.

In embodiments, the devices are designed to be deployed through natural orifices and lumens of the body in minimally invasive deployment procedures. For example, the devices may have a deployment shape suited for deployment through a natural lumen of the body. The devices also are designed to be retained in the body once implanted, such as by achieving a retention shape upon implantation or by anchoring within the body. In particular embodiments, the devices can be deployed through the urethra into the bladder and can overcome the forces of urination once implanted for retention in the bladder.

Once implanted, the devices can release one or more drugs over an extended period. The drug may be released by osmotic pumping through an opening in the device, by diffusing through a surface of the device, by diffusing from an opening in the device, or a combination thereof. The drug release may be continuous and in accordance with a pre-defined release profile.

In particular embodiments, the device includes at least two drug release portions, at least one release portion releasing drug at a different rate than another release portion. The release portions may achieve different release rates by having different configurations, by housing different drug formulations, or by employing different release mechanisms, among others or combinations thereof. The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

In embodiments, the devices are loaded with drugs in the form of a number of solid drug tablets, which may be smaller in size than conventional drug tablets. Because the devices control release of the drug into the body, the drug itself may include little or no excipients that control drug release. Instead, the excipients present in the drug tablets may be present primarily or completely to facilitate the tableting process or solubilization in vivo. Thus, the devices may provide a high drug payload on a volume or weight basis, yet the devices may be small enough for in vivo deployment in a minimally invasive manner.

In particular embodiments, the drug delivery device may deliver lidocaine or another cocaine analogue locally to the bladder over a relatively extended period for the treatment of a condition such as interstitial cystitis/painful bladder syndrome, neurogenic bladder, or pain. The lidocaine may be in solid form, such as in the form of a number of discrete drug tablets. Different forms of lidocaine, such as lidocaine base and lidocaine salts, e.g., lidocaine hydrochloride monohydrate, may be released from a single device via different release mechanisms to achieve a desired release profile.

The device may be implanted in a patient in a minimally invasive procedure and may deliver drug long after the implantation procedure has ended, both passively and locally. When implanted in the bladder, the device overcomes many deficiencies of conventional treatments. The present device can be implanted once and can release drug over an extended period without surgery or frequent interventions, reducing the opportunity for infection and side effects, increasing the amount of drug delivered locally or regionally to the bladder, and improving the quality of life of the patient during the treatment process.

The devices build upon those described in the following U.S. patent applications, which are incorporated by reference herein: U.S. application Ser. No. 11/463,956, filed Aug. 11, 2006; U.S. application Ser. No. 12/333,182, filed Dec. 11, 2008; U.S. application Ser. No. 12/538,580, filed Aug. 10, 2009; U.S. application Ser. No. 12/825,215, filed Jun. 28, 2010; U.S. application Ser. No. 12/825,238, filed Jun. 28, 2010, U.S. Provisional Application No. 61/241,277, filed Sep. 10, 2009, and U.S. Provisional Application No. 61/370, 902, filed Aug. 5, 2010.

I. Implantable Drug Delivery Devices

Embodiments of devices disclosed herein generally include at least one drug portion and at least one retention portion. The drug portion includes at least one drug and at least one drug housing for the drug. The drug housing at least partially shields the drug from direct exposure to the implantation site and may at least partially control release of the drug into the implantation site. Example drug portions, each of which is configured to release drugs in a different manner, are described below with reference to FIGS. 1-6. The retention portion retains the device in the body once implanted. For example, the retention portion may include a retention frame that assumes a retention shape to retain the device in the body or an anchor that anchors the device in the body. The device can be deployed into the body, such as through the urethra or another natural lumen of the body into the bladder or another body cavity. Once so implanted, the retention portion retains the device in the body by assuming the retention shape or anchoring therein, and the drug portions release drug into the implantation site over an extended period. A number of different drug portions can be associated with a single retention portion to achieve a desired drug release profile, as further described below. First, however, several drug portion configurations are described.

Figure 2:
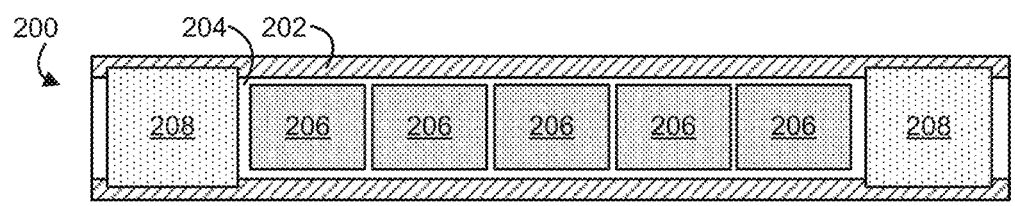
FIG. 2 is a cross-sectional plan view of an embodiment of a drug portion of a drug delivery device, the drug portion configured to release drug via diffusion.

Example drug portions are shown in FIGS. 1 and 2. Each of the drug portions 100, 200 includes a drug housing 102, which is formed from a single tubular wall. The housing 102 defines an internal drug reservoir 104 for housing the drug, and the drug 106 is positioned in the reservoir 104. Ends of the drug housing 102 are closed with sealing structures 108, which contain the drug therein. The configuration of the housing wall at least partially controls release of the drug from the drug reservoir into the implantation site. Example wall characteristics that affect the release rate include the permeability of the wall to water, the permeability of the wall to drug, the thickness of the wall, the porosity of the wall, and the presence or absence of passageways through the wall, such as openings, apertures, holes, or passing pores, among other characteristics or combinations thereof. For example, the drug portion 100 includes an aperture 110 for releasing the drug under osmotic pressure, while the drug portion 200 does not include an aperture and releases the drug via diffusion. The wall thus can be considered a release wall as the characteristics of the wall affect the release rate of the drug from the reservoir.

The drug portions 100 and 200 of FIGS. 1 and 2, and other examples herein, are described with reference to a drug housing formed completely from a single release wall, but a person of skill in the art would understand that the housing may be formed from any numbers of walls, all of which together shield the drug from the implantation site but only one or some of which constitute release walls. In other words, the drug need not be bounded on all sides by a single wall that affects release. Instead, the drug may be bounded by a group of walls, only one of which or a sub-set of which affect release. Additionally, the housing may have other shapes, including shapes that are not tubular or cylindrical. All of these configurations are within the scope of the present disclosure.

In some embodiments, the drug housing may be flexible so that the drug portion can be deformed during deployment. For example, the wall may be formed from a flexible material. The drug also may be in a flexible or workable form, such as in the form of a liquid, a semi-solid, a powder, or a number of individual solid drug tablets that can move with reference to each other, among others. As used herein, "liquid" drug forms include drugs in solution and other liquid forms; "semi-solid" drug forms include drugs in viscous emulsions or suspensions, gels, pastes, and other semi-solid forms; and "solid" drug forms include drugs in powder, rod, tablet, pellet, bead and other solid forms.

In some embodiments, the drug housing may be water-permeable. Typically, the wall is formed from a water-permeable material that permits water to diffuse into the drug housing along its entire length or a substantial portion thereof. The wall also may have one or more openings or passageways formed completely through its surface to permit water influx. Water passing into the drug housing may dissolve solid drug tablets loaded in the housing so that the drug can be released. Water passing into the drug housing also may create an osmotic pressure gradient within the housing that facilitates driving drug from the device through an aperture or other exit passageway.

The drug housing also permits the egress of drug, in either liquid or semi-solid form as implanted or following in vivo solubilization. The wall may be formed from a drug-permeable material that permits drug efflux through the drug housing along its entire length. The wall also may be formed from a material that is semi-permeable to the drug depending at least in part on the drug form. For example, the wall may be permeable to the drug in one form, such as a charged form, but not another form, such as uncharged form (e.g., base form versus salt form). The wall also may include one or more openings or passageways formed completely through it that permit drug to exit the drug housing.

In some embodiments, the wall is made of an elastic, biocompatible polymeric material. The material may be non-resorbable or resorbable. Example non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, and poly(siloxanes). Example resorbable materials, specifically biodegradable or bioerodible polymers, include synthetic polymers selected from poly(amides), poly(esters), poly (ester amides), poly(anhydrides), poly(orthoesters), polyphosphazenes, pseudo poly(amino acids), poly(glycerol-sebacate), poly(lactic acids), poly(glycolic acids), poly(lactic-co-glycolic acids), poly(caprolactones), poly(caprolactone) (PC) derivatives, amino alcohol-based poly(ester amides) (PEA) and poly (octane-diol citrate) (POC), and other curable bioresorbable elastomers. PC-based polymers may require additional cross-linking agents such as lysine diisocyanate or 2,2-bis($\varepsilon$-caprolacton-4-yl)propane to obtain elastomeric properties. Copolymers, mixtures, and combinations of the above materials also may be employed.

In particular embodiments, the wall may be formed from a material that is both water-permeable and flexible. Silicone is one example polymeric material that is flexible and can act as a water-permeable membrane when formed as a thin wall, with the permeability determined at least in part by the wall thickness. For example, a thin wall of silicone may have a thickness in the range of about 100 μm to about 1000 μm, although other wall thickness can be used. Further, a thin wall of silicone may be permeable to some drugs, depending on, for example, the porosity of the wall, the size of the drug molecule, its molecular weight, or its charge. For example, a thin wall of silicone may be permeable to lidocaine base but substantially impermeable to lidocaine hydrochloride monohydrate, due at least in part to the difference in charge and/or molecule size. For simplicity, a silicone wall is referenced throughout this disclosure, although a person of skill would understand that another material with comparable properties can be used. Examples of other suitable materials include medical grades of poly(vinyl chloride), polyolefins and polyether urethanes.

The size of the housing, including the thickness of the wall, may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device and/or may not have sufficient flexibility to permit delivery through a urethra or other narrow body lumen.

Figure 3:
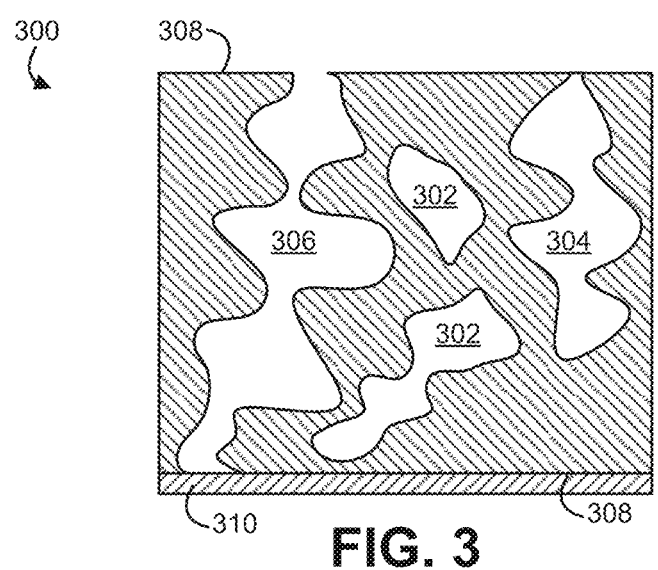
FIG. 3 is a cross-sectional plan view of a portion of a porous wall of a drug delivery device.

In some embodiments, the wall may be porous, meaning the wall may have one or more pores. A close-up cross-sectional view of a porous wall 300 is shown in FIG. 3. Pore types include isolated pores 302 that are encased completely within the wall 300 and penetrable pores that extend from a surface 308 of the wall into its interior. Penetrable pores may be non-passing pores 304 that terminate within the interior of the wall or passing pores 306 that extend completely through the interior, forming a defined passageway through the wall. The porous wall 300 may have a closed-cell structure, in which all of the pores are isolated or occluded, or an open-cell structure in which at least some of the pores interconnect to form passing pores extending between its inside and outside surfaces. An open-cell structure may contain dead-end or occluded pores, but at least some penetrable passing pores are present. In particular embodiments, a porous wall having an open-cell structure can be treated to mimic a closed-cell structure, such as by applying a coating or skin layer about its exterior surface, its interior surface, or both. An example is shown in FIG. 3, wherein the otherwise open cell-structure of the porous wall 300 has been treated with a coating 310 on one of the surfaces, blocking the passing pore 306 to form a closed-cell structure. The material used to form the skin layer may be the same as or different from the material used to form the porous wall. For example, the skin layer may be a polymeric material. A porous wall may have increased water- or drug-permeability in comparison to a non-porous wall, and a porous wall with an open-cell structure may have an increased permeability in comparison to a porous wall with a closed-cell structure.

As mentioned above, the wall may have one or more passageways formed completely through its surface, providing a path for water flow into and/or drug flow from the drug reservoir. The passageway may be an aperture formed completely through the wall, such as by drilling, punching, or molding. The term aperture is interchangeably used herein with the terms orifice, opening, and hole. The aperture may have a circular or other shape, whether extending directly through the wall, tapering slightly, or otherwise. An example aperture 110 is shown in FIG. 1. The passageway also may be a passing pore through a porous wall. An example passing pore 306 is shown in FIG. 3. Passing pores may tend to define tortuous passageways through the wall, while apertures may tend to define straight or tapered passageways through the wall. The wall may include a single passageway, an array of passageways positioned in a spaced configuration, or a multitude of passageways covering the wall along its entire length or in a particular area. Apertures may lend themselves to placement in discrete positions, while passing pores may lend themselves to covering larger areas, e.g., randomly or uniformly distributed throughout the wall structure.

The drug housing is loaded with the drug to form the drug portion. The drug may substantially fill the drug reservoir within the drug housing to maximize the drug payload deliverable from a small device, although filling is not necessary. The drug payload also may be flexible or workable as a whole so that the loaded drug portion can be deformed during device deployment. Liquid or semi-solid drug forms are inherently workable and may be suited for quick release following implantation. Solid drug forms may have an increased active drug content on a per volume basis in comparison to liquid and semi-solid drug forms, making better use of the space in the drug reservoir and permitting a reduction in the overall device size. Solid drugs also can be solubilized in vivo prior to release, such as with water directed through the wall and/or any passageways formed in the wall. Some solid drug payloads are flexible overall, including powdered drug payloads or payloads formed from individual drug tablets that can move with reference to each other. A flexible solid drug form also can be created directly within the drug housing by breaking a solid drug within the housing to form pieces that accommodate device movement. Such a technique may be employed for a solid drug that was extruded with the housing or that cured or solidified in the housing after being loaded into the housing in a liquid or workable state.

In the illustrated embodiments, the drug payload is in the form of a number of solid drug tablets that are shaped to align in a row, substantially filling the drug reservoir at least along its cross-section. The drug tablets are elongated and slender "mini-tabs" that are relatively small in comparison to conventional drug tablets, so that a drug portion loaded with a row of the drug tablets can pass through the urethra or another natural lumen of the body. Using solid drug tablets exploits the fact that drug tablets can be reliably manufactured with reproducible drug release characteristics, and yet device flexibility is not sacrificed, as the individual drug units can move with reference to each other one loaded. Embodiments of solid drug tablets and systems and methods of making them are described in the U.S. patent applications incorporated herein.

The drug formulation can include essentially any therapeutic, prophylactic, or diagnostic agent, such as one that would be useful to deliver locally to a body cavity or lumen or regionally about the body cavity or lumen. As used herein, the term "drug" with reference to any specific drug described herein includes its alternative forms, such as salt forms, free acid forms, free base forms, and hydrates. The drug may be a biologic. The drug formulation may consist only of the drug, or the drug formulation may include one or more pharmaceutically acceptable excipients, such as lubricants, viscosity modifiers, surface active agents, osmotic agents, diluents, and other non-active ingredients intended to facilitate manufacturing, loading handling, stability, dispersibility, wettability, and/or release kinetics of the drug.

In preferred embodiments, each drug tablet includes a relatively high weight fraction of the drug and a relatively low weight fraction of excipients. For example, each drug tablet may include more than 50% drug by weight, which permits loading a relatively small device with a therapeutically effective amount of drug. The release rate of drug from the device may be predominately controlled by the drug housing and may be altered by adjusting the housing characteristics, such as its thickness and permeability. Thus, the excipient content may be primarily selected to facilitate manufacturing and to achieve suitable solubility or dissolution characteristics, which in conjunction with the structural and material characteristics of the drug housing determine the drug release profile of the device. For example, the formulation of the drug and excipients may be selected so that the drug tablets can be solubilized once implanted. The formulation also may be selected to improve its apparent solubility in the implantation environment, such as its apparent solubility in urine within the bladder.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, while low solubility drugs may be suited for release via diffusion through the wall or passageway in the drug housing. Thus, the drug may be formulated to have a high or low solubility depending on the intended release mode.

In particular embodiments, the drug may be a local anesthetic agent, such as a cocaine analogue, that is delivered locally to the bladder over a relatively extended period for the treatment of a condition such as interstitial cystitis/ painful bladder syndrome, neurogenic bladder, or pain such as post-operative pain, among others. In particular embodiments, the local anesthetic agent is lidocaine, such as lidocaine hydrochloride monohydrate or lidocaine base. The local anesthetic agent also can be any other aminoamide, aminoester, or other local anesthetic agent, or the drug can be a drug other than a local anesthetic agent. Representative examples of other drugs are described below, and combinations can be employed.

Once implanted, the drug may be released from the drug housing. The drug may be released via osmotic pumping through an aperture or passing pore in the drug housing, via diffusing across the wall of the drug housing, via diffusing directly through an aperture or passing pore of the housing, or a combination thereof. The release may be delayed or modulated by altering characteristics of the drug portion. Examples are described below with reference to FIGS. 1-6.

FIG. 1 illustrates a drug portion that is configured to operate as an osmotic pump. The drug portion 100 includes a wall 102 that is readily permeable to water but not drug 106 and a drug 106 that is highly water-soluble but cannot readily diffuse through the wall 102. After the device is implanted, water or urine permeates through the wall 102, enters the reservoir 104, and solubilizes the drug 106. An osmotic pressure gradient begins developing between the interior and exterior of the drug housing, and once sufficient pressure is achieved, solubilized drug is released from the reservoir 104 through the aperture 110 at a controlled rate, driven by osmotic pressure in the reservoir 104. Such a release mode is referred to herein as "osmotic release" or "osmotic pumping". One example of a wall/drug combination suited for osmotically driven release is a thin silicone wall associated with solid drug tablets of lidocaine hydrochloride monohydrate.

The drug portion 100 may exhibit an induction period while a sufficient volume of drug is solubilized to achieve the osmotic pressure gradient. Subsequently, the drug portion 100 may exhibit a zero-order release rate for an extended period, followed by a reduced, non-zero-order release rate over a decay period. The delivery rate is affected by the surface area of the wall 102; the thickness of the wall 102; the permeability to water of the material used to form the wall 102; the shape, size, number and placement of the apertures 110; and the dissolution profile of the drug 106, among other factors. For example, a relatively thinner wall 102 may be used to create a relatively faster osmotic pump than a relatively thicker wall 102, as a thinner wall 102 may be relatively more permeable to water. As another example, the size and number of apertures 110 can be varied to achieve a selected release rate, although apertures 110 that are too large may permit diffusive transport and apertures 110 that are too small or too far apart may result in hydrostatic pressure build-up within the reservoir 104. Suitable apertures 110 may be between about 20 μm and about 500 μm in diameter, among others. Representative examples of osmotic pump designs, and equations for selecting such designs, are described in U.S. patent applications incorporated herein and in Theeuwes, *J. Pharm. Sci.,* 64(12):1987-91 (1975).

Osmotic pumping may be the dominant drug release mechanism for a highly water-soluble drug released from a drug housing that has a water-permeable wall and an aperture, such as lidocaine hydrochloride monohydrate released from drug housing that has a silicone wall and an aperture. Diffusion through the wall or the aperture may play a minor role in drug release, depending on the drug-permeability of the wall and the size of the aperture. Although osmotic release is feasible for highly water soluble drugs, many drugs have low solubility to water and therefore are not suited for such a release mechanism. In such cases, the drug portion may be configured to release the drug via diffusion.

FIG. 2 illustrates an embodiment of a drug portion 200 that releases drug 206 via diffusion across the drug portion wall 202, also referred to herein as "trans-wall diffusion". After the device is implanted, water or urine permeates through the wall 202, enters the reservoir 204, and solubilizes the drug 206. The drug 206 then diffuses directly through the wall 202 at a controlled rate, due to a drug concentration gradient between the interior and the exterior of the device 200. One example of a wall/drug combination suited for trans-wall diffusive release is a thin silicone wall associated with solid drug tablets of lidocaine base.

The drug portion 200 may exhibit a zero-order release rate for an extended period, followed by a reduced, non-zero-order release rate over a decay period. Zero-order release may begin relatively quickly, as the drug 206 may be immediately available to diffuse across the wall 202 once solubilized. The delivery rate is affected by the surface area of the wall 202; the thickness of the wall 202; the permeability to water and drug of the material used to form the wall 202; the charge or particle size of the drug 206; and the dissolution profile of the drug 106, among other factors. For example, a drug may be able to diffuse through a wall in a charged state but not in an uncharged state, due at least in part to a difference in molecule size. One example is lidocaine, which can diffuse through a thin silicone wall when formulated as a base but not as a salt. In particular, lidocaine base may diffuse through a thin silicone wall at a zero-order release rate with minimal initial lag time, as described below in Example 1. A therapeutically effect amount of lidocaine may be delivered in this manner.

In other embodiments, the drug portion may release drug via diffusion through one or more apertures or passing pores. For example, in FIG. 1 the drug 106 may be released via diffusion directly through the aperture 110, or in FIG. 3 the drug may be released via diffusion directly through the passing pore 306 (if the skin layer 310 is omitted). The term "diffusion" applies to both, as well as trans-wall diffusion, unless a particular one is expressly specified. Although only one aperture 110 and one passing pore 306 are shown, a number or combination of apertures or passing pores can be used, which may affect the overall release rate attributable to diffusion.

Diffusion may occur as an alternative to or in addition to another release mode, such as osmotic pumping. Whether the addition of passageways increases the release rate may vary depending at least in part on the configuration of the wall and the formulation of the drug. For example, the addition of passageways to a wall that readily diffuses a drug may not increase the release rate associated with trans-wall diffusion. One example is a thin silicone wall that readily diffuses lidocaine directly through its surface, such that additional passageways only marginally increase the local release rate. As another example, the addition of passageways to a wall that is readily permeable to water may not increase the release rate associated with osmotic pumping. One example is a thin silicone wall that is readily permeable to water.

As shown in FIG. 3, the drug portion also may include a porous wall 300 with a closed-cell structure, which may affect the release rate by increasing the permeability of the wall to water or drug. A wall that is more water-permeable may permit greater water influx to achieve faster osmotic pumping, while a wall that is more drug-permeable may permit greater drug efflux to achieve faster diffusive transport. The extent to which non-passing pores affect the permeability of the wall depends on, for example, the permeability of the wall without the non-passing pores and the solubility or dissolution rate of the drug. For example, the addition of non-passing pores to an otherwise non-porous wall that is readily water permeable may not affect the permeability of the wall to water. A particular example is a thin silicone walls that is already permeable to water. As another example, the addition of non-passing pores to an otherwise non-porous wall that is readily permeable to a drug may not affect the permeability of the wall to the drug. A particular example is a thin silicone wall that is readily permeable to lidocaine base. For the purposes of this disclosure, the term "non-porous" wall indicates the wall does not include an open- or closed-cell porous structure.

Figure 4:
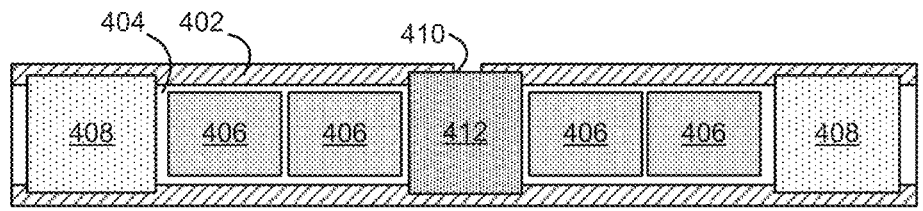
FIG. 4 is a cross-sectional plan view of an embodiment of a drug portion of a drug delivery device, the drug portion including a plug configured to delay the onset of drug release.
Figure 5:
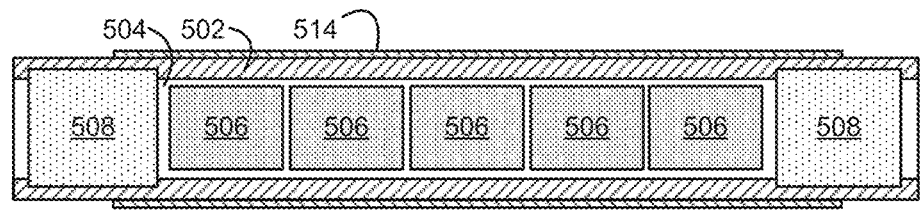
FIG. 5 is a cross-sectional plan view of an embodiment of a drug portion of a drug delivery device, the drug portion including a sheath configured to modulate drug release.
Figure 6:
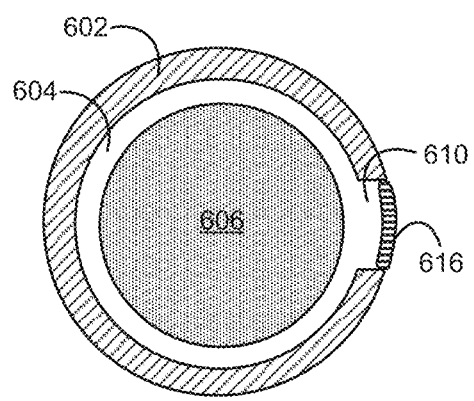
FIG. 6 is a cross-sectional side view of an embodiment of a drug portion of a drug delivery device, the drug portion including an orifice enclosed with a timing membrane.

FIGS. 4-6 illustrate drug portions with degradable timing structures that delay the initial onset of drug release following implantation. The degradable timing structures are formed from materials that biodegrade, erode, or dissolve in vivo, such as in response to contact with water. The degradable timing structures initially block or prevent release of the drug, such as by preventing water from entering the drug housing to solubilize the drug or by preventing drug from exiting the housing through the wall or one or more passageways. At some point after implantation, the degradable timing structures partially or completely dissolve or degrade, permitting water egress and/or drug release. Thereby, initial release of the drug is delayed. The length of the delay may be influenced by the properties of the degradable timing structure, such as its materials of construction, size, and shape.

FIG. 4 illustrates an embodiment wherein the degradable timing structure is a degradable timing plug 412 positioned within the drug reservoir 404 between the drug 406 and at least one passing pore or aperture 410. The degradable timing plug 412 blocks release of solubilized drug through the passageway, whether by osmotic pumping or diffusion, until the degradable timing plug 410 has degraded. The degradable timing plug 412 may be made from various biocompatible materials known in the art that are bioresorbable or otherwise degradable in vivo, such as PLG, PGA, PLGA, a lipid, or a polysaccharide, among others.

FIG. 5 illustrates an embodiment wherein the degradable timing structure is a degradable coating 514 positioned about a least a portion of the wall 502. The degradable coating 514 prevents water or drug from passing through the wall 502, preventing both osmotic pumping and diffusion until the degradable coating 514 has degraded. The degradable coating 514 may be, for example, a bioresorbable film.

FIG. 6 illustrates an embodiment wherein the degradable timing structure is a degradable membrane 616 associated with a passageway, such as a passing pore or aperture 610. The degradable membrane blocks drug release through the passing pore or aperture 610, whether by osmotic pumping or diffusion, until the degradable membrane 616 has degraded. The degradable membrane 616 may be formed, for example, of a resorbable synthetic polymer (such as polyester, a poly(anhydride), or a polycaprolactone) or a resorbable biological material (such as cholesterol, other lipids and fats). Combinations of these degradable timing structures may be used along any portion of the drug housing. For example, one or more of the degradable timing structures may be associated with only a portion of the drug housing or a subset of the passageways, reducing the release rate during an initial period by limiting release from a portion of the device.

Drug release also may be modulated in other manners. For example, a sheath may be positioned over a portion of the wall to reduce the release rate, such as by reducing the osmotic surface area of the wall or by reducing diffusion through the wall. The coating or sheath may cover all or any portion of the wall, may be relatively uniform, or may vary in thickness, size, shape, position, location, orientation, and materials, among others and combinations thereof. An example coating for a silicone wall may be formed from parylene, while an example sheath may be formed from a polymer such as polyurethane or curable silicone, or another biocompatible coating or sheath material known in the art. In some embodiments, the coating or sheath may be positioned on the wall between an aperture and an end of the drug portion, so that water permeating through the wall adjacent to the end is driven through the portion of the housing covered by the sheath, reducing or avoiding isolation or stagnation of the drug under the sheath.

The drug release rate from a drug portion may be adjusted by altering the characteristics of the wall, such as its thickness or surface area, with protrusions such as ribbing or nubs. Increasing the effective surface area may increase the osmotic surface area in contact with water or urine in the implantation site, which may increase water permeation through the drug housing. On the other hand, increasing the surface area may increase the thickness of the drug housing in certain areas, which may decrease water or drug permeation through the housing. The size, shape, and location of the ribbing or protrusion can be selected to increase or decrease water or drug permeation as desired to achieve an overall desired release rate.

Figure 7:
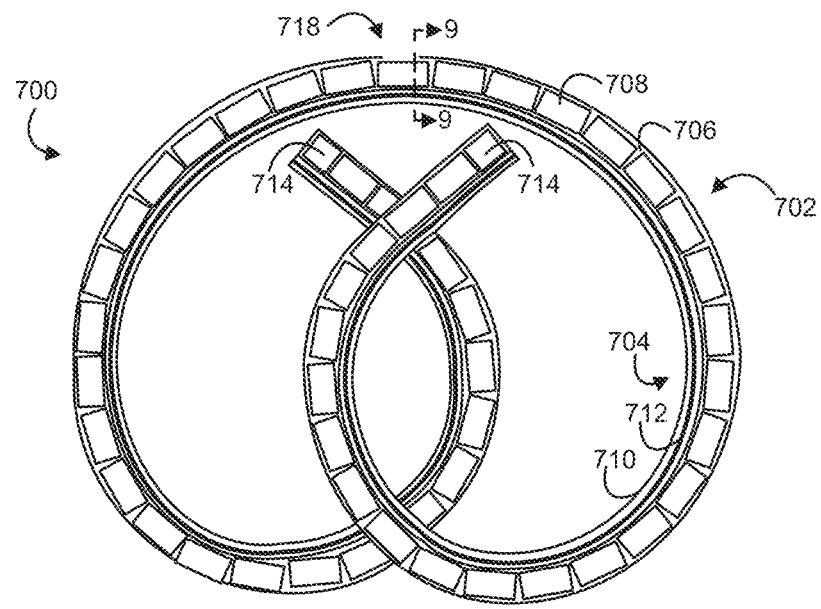
FIG. 7 is a cross-sectional plan view of an embodiment of a drug delivery device.
Figure 8:
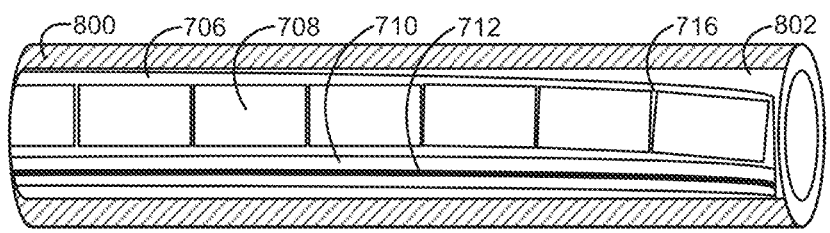
FIG. 8 is a cross-sectional plan view of the drug delivery device shown in FIG. 7, illustrating the drug delivery device inside a deployment instrument.

As mentioned above, an implantable drug delivery device can be formed by associating a drug portion with a retention portion. An example embodiment is shown in FIG. 7, wherein the device 700 includes a drug portion 702 and a retention portion 704. The drug portion 702 includes a drug housing 706 that houses a drug 708 and the retention portion 704 includes a retention frame housing 710 that houses a retention frame 712. The drug housing 706 and retention frame housing 710 are axially aligned with reference to each other and are formed from a flexible material, which permits moving the device 700 between the retention shape shown in FIG. 7, and a deployment shape shown in FIG. 8. "Retention shape" generally denotes any shape suited for retaining the device in the intended implantation location, including but not limited to the coiled shape shown in FIG. 7 that is suited for retaining the device in the bladder, while "deployment shape" generally denotes any shape suited for deploying the drug delivery device into the body, including the linear or elongated shape shown in FIG. 8 that is suited for deploying the device through a working channel 802 of a deployment instrument 800 positioned in the urethra or other natural lumen.

The drug housing 706 houses a drug in the form of a number of solid drug tablets 708, which are aligned within the drug housing 706 in a serial arrangement and are enclosed within the drug housing 706 with sealing structures, such as plugs 714, that close entry openings on opposite ends of the drug housing 706. Interstices 716 or breaks formed between adjacent drug tablets 708 permit the drug tablets 708 to move with reference to each other so that the device 700 is flexible despite being loaded with drug in solid form.

The drug tablet may be a mini-tablet, which is substantially cylindrical in shape, having end faces that are relatively planar or flat and a side face that is substantially cylindrical. The shape permits piecewise flexibility of the device while limiting the volume or space within the drug housing that is devoted to the interstices or breaks. Thus, the device can be substantially filled with solid drug while retaining its flexibility. In some embodiments, the drug tablets are relatively tall and slender, unlike conventional drug tablets that tend to be short and squat. The drug tablets may be tall enough to retain their orientation once loaded in the drug reservoir, with reduce tipping or rolling. On the other hand, the drug units may be short enough to provide enough interstices or breaks so that the device can flex or move along its length. In particular, each drug unit may have a length that exceeds its width, meaning an aspect ratio of height:width that is greater than 1:1. Suitable aspect ratios for the drug units may be in the range of about 3:2 to about 5:2, although other aspect ratios are possible. The mini-tablet has a diameter, extending along the end face, in the range of about 1.0 to about 3.2 mm, such as between about 1.5 and about 3.1 mm. The mini-tablet 312 has a length, extending along the side face 328, in the range of about 1.7 mm to about 4.8 mm, such as between about 2.0 mm and about 4.5 mm.

The drug portion 702 can have any combination of the characteristics or configurations described above with reference to FIGS. 1-6 to achieve the desired release profile, meaning the aperture 718 may be provided, omitted, substituted with a passing pore, or augmented with additional apertures or passing pores; the housing may have a porous wall with an open-cell structure or a closed-cell structure; one or more degradable timing structures or release modulating structures may be associated with the housing, or any combination thereof.

The retention frame housing 710 houses a retention frame 712, which may be an elastic wire that can deformed into the deployment shape for insertion and can return to the retention shape upon exiting the deployment instrument, either spontaneously or through manual intervention. An example retention frame 712 may be formed from a superelastic and/or shape-memory material, such as nickel-titanium alloy (e.g., Nitinol) or titanium-molybdenum alloy (e.g., Flexium), or from a low modulus elastomer, such as polyurethane, silicone, styrenic thermoplastic elastomer, or poly(glycerol-sebacate) (PGS). Other suitable materials, and combinations or materials, can be used. In the retention shape, the retention frame may have an elastic limit, modulus, and/or spring constant that impedes the device from assuming the deployment shape, limiting or preventing expulsion of the device from the body under expected forces, such as the forces of urination. The illustrated shape is merely one example of a suitable shape, and other shapes may be used that provide a spring constant without which the frame would significantly deform under the forces of urination. For example, the retention frame may have a spring constant in the range of about 3 N/m to about 60 N/m, or more particularly, in the range of about 3.6 N/m to about 3.8 N/m. Such a spring constant may be achieved by increasing the diameter of the frame, increasing the curvature of one or more windings, coils, or curves of the frame, adding additional windings, coils, or curves to the frame, or combinations thereof.

Figure 9:
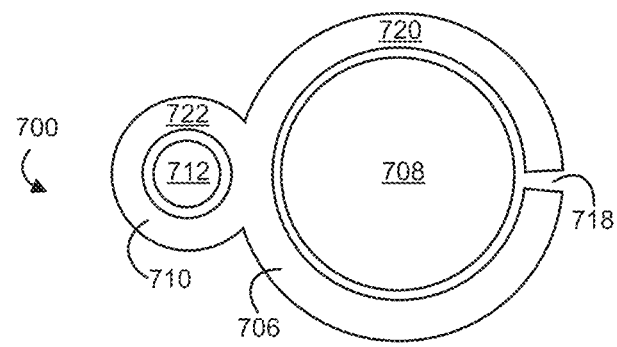
FIG. 9 is a cross-sectional side view of the drug delivery device shown in FIG. 7.

As shown FIG. 9, which is a cross-sectional view of the device 700 taken along line 9-9 in FIG. 7, the drug housing 706 and retention frame housing 710 are generally walls that define internal lumens for housing the corresponding device components. One wall 720 defines the drug housing 706, and another wall 722 defines the retention frame housing 710. The walls 720, 722 are integrally formed together into a single device body, and the material used to form the device body may be elastic or flexible to permit moving the device 700 between deployment and retention shapes. The illustrated walls 720, 722 are substantially cylindrical tubes that define substantially cylindrical lumens, the drug reservoir lumen having a relatively larger diameter than the retention frame lumen.

Other device configurations are within the scope of the present disclosure, some of which are further described in co-pending patent applications incorporated by referenced herein. For example, the two portions can have other relative orientations with reference to each, including orientations where one portion is axially aligned with the other, one portion is spaced about from the other, one is wrapped about the other, or one portion is coincident with the other. The two portions can be integrally formed with each other or can be attached to each other, either intermittently or along their entire length. The two portions can have different relative lengths and dimensions, with one portion being shorter than the other, one portion being longer than the other, one portion having a larger cross-section than the other, or one portion having a smaller cross-section than the other. Either portion can have a different shape other than the illustrated cylindrical shape, a different numbers of walls other than the illustrated single tubular wall, and a different type of wall other than the flexible wall. The two housings may not be integrally formed into to a device body, instead being separately constructed and assembled, and the two lumens need not be discrete from each other, instead co-mingling either in whole or in part.

The drug tablets may be aligned in any arrangement other than a serial arrangement, depending on the configuration of the drug housing. The drug tablets may fill any portion of the drug housing other than the entire drug housing as illustrated. A filling material such as silicone adhesive can be used to fill any portion of the drug housing that is not loaded with drug tablets, or air may be used, increasing the buoyancy of the device. The composition of the drug tablets may be the same or may vary along the device. The drug also may be in forms other than a drug tablet, such as liquid, semisolid, or solid forms.

Figure 10:
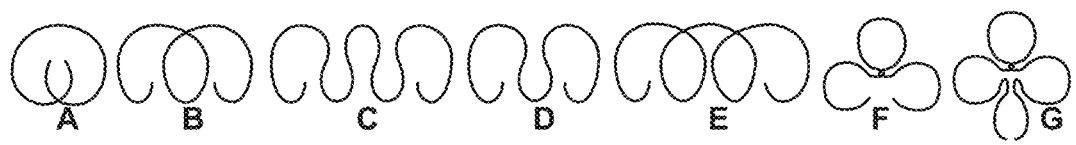
FIG. 10 illustrates example shapes for a retention frame of a drug delivery device.
Figure 10:
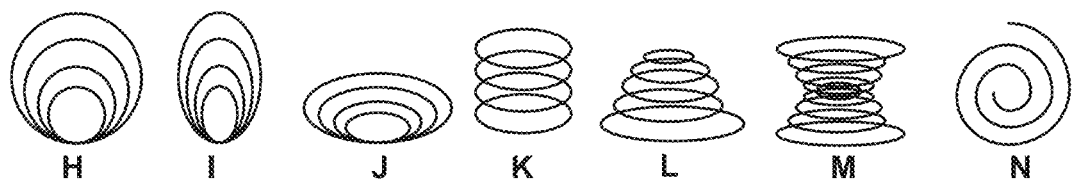

The retention portion can have other configurations that cause the device to be retained in the body, either by the retention portion assuming a retention shape, by the retention portion causing the drug portion to assume a retention shape, or by the retention portion anchoring the device in the body. In embodiments in which the retention portion includes a retention frame within a retention housing, the retention housing may have other configurations, such as a coating applied to the retention frame to soften its exterior. The retention frame may have other shapes that can be elongated or otherwise deformed for deployment, and once implanted exhibit a sufficient spring constant, elastic limit, and/or elastic modulus to resist excretion in response to expected forces. Examples are shown in FIG. 10, wherein Examples A through G illustrate frames comprising one or more loops, curls, or sub-circles, connected either linearly or radially, turning in the same or in alternating directions, and overlapping or not overlapping, and wherein Examples H through N illustrate frames comprising one or more circles or ovals arranged in a two-dimensional or a three-dimensional configuration, the circles or ovals either closed or opened, having the same or different sizes, overlapping or not overlapping, and joined together at one or more connecting points. One or both of the retention frame and retention housing may be omitted, in which case the retention portion may be components of the drug portion itself, which may assume or may be deformed into a retention shape, or the retention portion may be an anchor associated with the drug portion. Examples of alternative configurations are described in the U.S. patent applications incorporated by reference herein.

Figure 11:
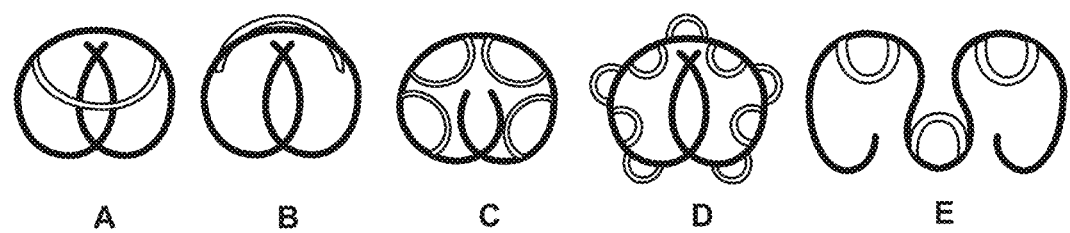
FIG. 11 illustrates example configurations for drug delivery devices having at least one drug delivery portion and a retention frame portion.
Figure 11:
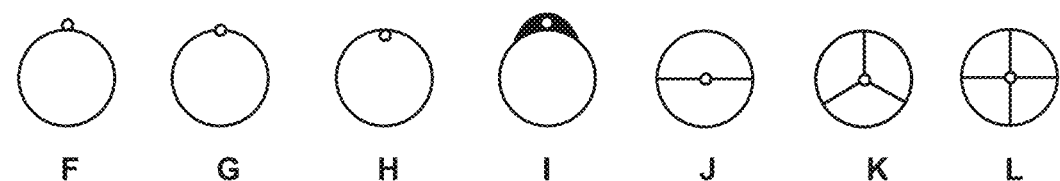
Figure 11:
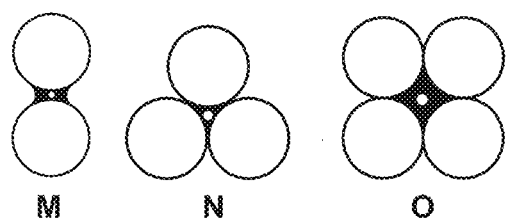

Additional examples of alternative configurations are shown in FIG. 11. As shown in Examples A through E, one or a number of drug portions may be attached to an intermediate region or ends of the retention portion, the drug portion lying within or beyond the perimeter of the retention portion with its ends attached to or overlapping the retention portion. Examples F through O show cross-sections of devices having drug and retention portions that are at least partially aligned. In other words, the drug portion may extend along a portion or the entire length of the retention portion, substantially parallel or coincident with the retention portion. As shown in Examples F through I, the retention frame wire may extend along either an exterior surface of the wall of the drug portion, along an interior surface of the wall, through the wall, or within a reinforced area inside or outside of the wall. As shown in Examples J through L, the retention frame also may be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs. The web may be formed from the same material as the tube, or from a material having a different permeability to water or urine, depending on the embodiment. As shown in Examples M through O, the elastic wire may be associated with multiple tubes, extending along or between the tubes. The elastic wire may be embedded in a reinforcement area that joins together multiple discrete tubes. The drug portion also may constitute the retention portion, such as in cases in which the drug portion comprises tubing formed in a configuration having a sufficient spring constant to retain the device in the body, as described above. Any of the above-described variations can be combined to achieve a device of the desired characteristics.

In particular embodiments, the drug delivery device includes at least two discrete or segregated drug portions associated with a single retention portion. The drug portions may be separate drug housings each associated with the retention portion, or the drug portions may be separate areas within a single drug housing that is associated with the retention portion. FIG. 11 illustrates example drug portions with separate housings in Examples C through E. FIG. 11 also illustrates example drug portions that are segregated areas within a single housing in Examples J through L. FIG. 11 also illustrates drug portions in Examples M through O that could have either configuration depending on materials and construction.

Figure 12:
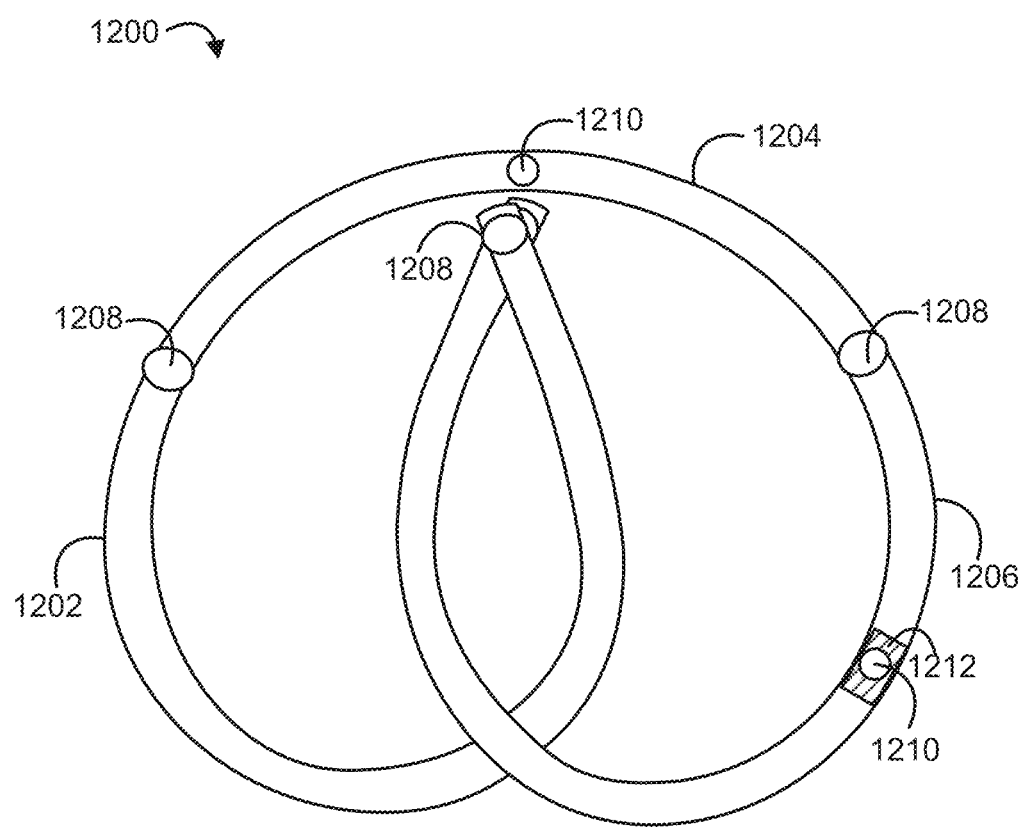
FIG. 12 is a plan view of another embodiment of a drug delivery device.

FIG. 12 is a plan view of another embodiment of a drug delivery device 1200 having a drug housing that is partitioned into multiple segregated drug portions. Three drug portions 1202, 1204, and 1206 are shown, although any number may be used. Each drug portion is defined by a portion of the wall of the drug housing and at least one partition structure 1208, which separates the drug portion from an adjacent drug portion. The partition structure 1208 may be a plug inserted into the housing, such as a cylinder, sphere, or disk, among others, which is secured in place due to its size or with an adhesive. The partition structure 1208 also may be a portion of the housing formed directly therein, such as by molding. For example, the webs shown in Examples J through L of FIG. 11 are partition structures that segregate drug portions along the length of the device.

A device with at least two discrete portions may be suited for controlled release of at least two drug payloads from a corresponding number of drug reservoirs. The two discrete portions may have the same configurations or different configurations, such one or any combination of the configurations described above with reference to FIGS. 1-6. The two drug payloads may be the same as each other or may differ from each other with reference to content, such as active ingredient content or excipient content; form, such as salt form or base form; state, such as liquid, semi-solid, or solid state; among others or combinations thereof. Thus, the two discrete portions may release the two drug payloads at the same time or at different times, at the same rate or at different rates, via the same release mechanisms or different release mechanisms, or any combination thereof.

For example, one drug portion may be configured to release its drug payload relatively quickly after implantation and another drug portion may be configured to experience an induction time before beginning release, or a combination thereof. The onset of release of two payloads in different drug portions can be staged. Examples of quick release drug portions include a drug portion that operates as a relatively fast-acting osmotic pump, such as a silicone tube having a relatively thinner wall, a drug portion that is loaded with drug in a quick release form, such as liquid form or a specially formulated solid form, a drug portion associated with a relatively fast-acting degradable timing structure, or combinations thereof. Thus, the device may release drug during an initial, acute phase and during a maintenance phase.

As another example, one drug portion may be configured to release its drug payload at a relatively faster rate than the other drug payload. For example, one drug portion may house a drug payload with low water solubility for diffusive release that is initiated relatively soon after implantation, and another drug portion may house a drug payload that is highly water soluble for osmotic release after an induction period. As another example, one drug portion may house a drug payload in a liquid state for quick release through an aperture having a fast-acting degradable timing membrane, and another drug portion may house another drug payload of solid tablets for slow release following solubilization in vivo. As still another example, one drug portion may have a relatively solid wall while another drug portion may have a number of apertures or pores formed through its wall, which may increase the release rate due to diffusion, or a closed-cell porous wall, which may increase the release rate due to increased permeation of water or drug through the wall.

The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

In embodiments, one or more of the drug portions can be left empty to improve device buoyancy. Such drug portions may be formed from or coated with materials that exhibit low permeability to air and water to reduce water ingress and air egress.

The total volume of the drug portions is sufficient to contain all the drug needed for local or regional delivery over the course of a single treatment, reducing the number of procedures needed to treat a particular condition.

One particular example of a device is shown in FIG. 12, which illustrates a device 1200 that includes three discrete drug portions 1202, 1204, 1206, which release three different payloads of lidocaine in accordance with three different release profiles. Each drug portion includes lidocaine within a drug housing formed from a thin silicone wall. One or more of the lidocaine drug portions may be in solid form, such as tablets. The thin silicone wall is permeable to water and to lidocaine base, but not lidocaine hydrochloride monohydrate, due at least in part its charge and/or molecular size. It is noted that drug tablets are not shown in FIG. 12 for clarity.

The first discrete portion 1202 houses solid drug tablets of lidocaine base for release predominately via trans-wall diffusion. The first discrete portion 1202 does not include an aperture. In operation, water permeates through the wall into the housing, solubilizing the low water soluble lidocaine. The solubilized drug is immediately available to diffuse through the wall in a controlled manner. The release rate may be relatively zero-order for an extended period, such as a period of days or weeks, followed by a period of decay.

The second discrete portion 1204 houses solid lidocaine hydrochloride monohydrate, e.g., in the form of tablets, for predominately osmotic release. The second discrete portion 1204 includes at least one aperture 1210. In operation, water permeates through the wall, solubilizing the highly water soluble lidocaine tablets to create an osmotic pressure gradient. Once sufficient pressure has developed, the drug is pumped from the device through the aperture 1210 in a controlled manner. The release rate may exhibit an initial induction period while the osmotic pressure gradient develops, such as a period of several hours, followed by relatively zero-order for an extended period, such as a period of days or weeks, followed by a period of decay. Diffusion through the wall may be minimal due to the poor permeability of silicone to lidocaine hydrochloride monohydrate. Diffusion through the aperture may contribute to the release rate, although such diffusion can be controlled through appropriate selection of the aperture size.

The third discrete portion 1206 has a degradable timing structure configured to delay the onset of drug release. In the illustrated embodiment, the third discrete portion 1206 has a similar configuration to the second discrete portion 1204, housing lidocaine hydrochloride monohydrate tablets for osmotic release from an aperture 1210. The third discrete portion 1206 also includes a degradable plug 1212 positioned below the aperture 1210 that initially blocks ingress or egress. At some point after implantation, the degradable plug 1212 partially or completely dissolves or degrades, permitting drug egress through the aperture. It should be noted that the third discrete portion 1206 could have other configurations suited for use with other degradable timing structures, such as a degradable timing coating.

By combining multiple distinct drug portions 1202, 1204, 1206 in a single device, the 1200 may exhibit a desired release profile of lidocaine. The release profile from the device 1200 as a whole may be the sum of the release profiles of the three discrete portions 1202, 1204, 1206, with the first portion 1202 exhibiting minimal lag time before the onset of release, the second portion 1204 exhibiting a short induction period as the osmotic pressure gradient develops, and the third portion 1206 exhibiting a longer delay before onset as the degradable structure dissolves or degrades. Once release begins from any one portion, the release rate may be relatively zero-order for an extended period, followed by a period of decay. It should be noted that the three discrete portions 1202, 1204, 1206 are examples, and that any number or combination of discrete portions may be used to achieve the desired release profile.

Because the different drug portions 1202, 1204, 1206 are merely segregated areas within in a single tubular housing, the device 1200 advantageously may be relatively simple to construct and deploy, and yet the different drug portions exhibit different release profiles due to the different drug payloads, aperture placement, and degradable timing structures. In other embodiments in which the drug portions 1202, 1204, 1206 use, for example, walls of different materials, thicknesses, or porous cell structures, the housing may vary along its length or separate drug housings may be used, as exemplified in FIG. 11. Thus, controlled release may be achieved in a range of manners.

In addition to releasing drug via multiple different release mechanisms, the device 1200 has a slightly different shape and configuration than the device 700 shown in FIG. 7. For example, the ends of the device 1200 are relatively straighter than the ends of device 700, as the retention frame of the device 1200 has relatively straight end portions, while the retention frame 712 of the device 700 has relatively curved end portions. A retention frame with relatively straight end portions have been discovered to be beneficial in that they may be less likely to puncture the housing during drug loading and thereafter, reducing the risk of device failure after implantation. However, either retention frame shape can be used.

Furthermore, when the device is in the retention shape, the retention portion may have any orientation with reference to the drug portion, lying either inside, outside, above, or below the drug portion or moving with reference to the drug portion as the device moves through the implantation site. For example, the device 700 includes a retention portion that lies inside the perimeter of the drug portion, while the device 1200 includes a retention portion that lies below the drug portion (such that the retention portion is not visible in FIG. 12). A particular orientation between the two portions can be maintained by filling the retention frame housing with a filling material, such as a silicone adhesive, after the retention frame is loaded. The filling material may cure or solidify to prevent movement of one portion with reference to the other. Other means of maintaining the orientation of the retention portion with reference to the drug portion also can be used.

The aperture may be positioned inside the perimeter of the device, outside of the perimeter of the device, or an upper or lower plane of the device. For example, the device 700 includes an aperture 718 located on an outside perimeter of the device, while the device 1200 includes an aperture 1208 located on an upper plane of the device. An aperture positioned on the inside perimeter or on the upper or lower plane of the device advantageously may be less likely to become positioned directly adjacent to a portion of the implantation site, such as the bladder wall, delivering a large quantity of drug to one particular location. The aperture also may be formed in a groove or indent defined between the walls of the drug housing and the retention frame housing, so that the walls serve as bumpers that impede the aperture from becoming positioned directly adjacent to the implantation site. For example, the aperture 718 of the device 700 could instead be formed in a groove or indent between the walls 720 and 722.

For ease of manufacturing, the aperture may be formed through the wall of the drug housing on an opposite side from the retention housing, as shown in FIG. 9. When the aperture is positioned opposite from the retention housing, it may be desirable to secure the retention portion below the device as described above, so that the aperture becomes positioned above the device, as shown in FIG. 12, reducing the risk of the aperture becoming positioned on the outside perimeter of the device. However, other configurations are possible, including any combination of the configurations shown in FIG. 7 and FIG. 12.

II. Methods of Making Implantable Drug Delivery Devices

The implantable drug delivery devices described herein can be formed in a variety of manners. One method of making the device includes (i) forming one or more drug portions, (ii) forming a retention portion, and (iii) associating the one or more drug portions with the retention portion. A drug portion may be formed by forming a drug housing and loading the drug housing with drug. The retention frame portion may be formed by forming a retention frame housing and loading a retention frame into the retention frame housing. Associating the drug portion with the retention portion may include attaching the two portions to each other, such as by integrally forming the two housings together or by subsequently attaching the two housings with an adhesive or other suitable attachment means. These steps may be performed in other orders, including iteratively and/or simultaneously.

One or both of the drug housing and the retention frame housing may be formed by injection molding, compression molding, extrusion molding, transfer molding, insert molding, thermoforming, casting, among others or combinations thereof. The two housings may be molded or extruded together into a single device body of the type shown in FIG. 9, in which case the housings may be associated with each other as they are formed. Separate construction and assembly of the two housings also is contemplated. Other techniques also may be employed. For example, the retention frame housing may be over-molded over the retention frame.

Once the drug housing is formed, the drug tablets are loaded into the drug housing. Solid drug tablets may be loaded in an elongated drug housing by positioning the tablets near an entry into the housing and driving the tablets into the housing using pressurized gas, such as by depressing a syringe of air in fluid communication with the device. Once loaded, the drug tablets may be sealed in the drug housing, such as by plugging or sealing ends of the drug housing. Solid drug tablets can be made using known drug tablet manufacturing processes, such as direct compression and molding. Particular methods of making and loading drug tablets are described in U.S. Application Publication No. 2010/0331770, which is incorporated by reference herein.

In embodiments in which the device is configured to release drug in accordance with multiple different release profiles, multiple discrete different drug housings may be formed, loaded, and associated with the retention portion. A single drug housing also may be partitioned into multiple discrete drug reservoirs, each of which is loaded with drug. For example, the elongated tubular drug housing of FIG. 12 may be partitioned by positioning one or more partition structures within the drug reservoir lumen in an alternating fashion with the loading of the drug tablets. The tubular housing also may be partitioned along its length, such as by molding or extruding the housing to include a web running along the length of its interior.

One or more apertures may be formed in the drug housing, such as by laser drilling, laser ablation, mechanically punching, or molding with an indenter, either before or after the drug is loaded into the tube. The drug housing also may be made porous. Porous elastomeric structures can be generated using any suitable process known in the art, including by adding a pore-forming agent into the polymer or a polymer precursor in solution. Suitable pore-forming agents include gas-producing agents, such as sodium bicarbonate, and water-leachable, polymer-insoluble additives, such as poly(ethylene glycol) (PEG) and sorbitol. A skin layer may be positioned on the porous housing, on its exterior surface, its interior surface, or both, to form a closed-cell structure.

One or more release controlling structures, such as a sheath or coating, may be placed over at least a portion of the surface of the drug portion to control the rate of release of the drug, such as by altering the permeability of the housing wall to water or to the drug.

To control the initial time of release of the drug from one or more of the apertures, a bioresorbable plug may be positioned within the housing adjacent to the aperture, or a degradable membrane may be positioned over or in the aperture. Degradable membranes may be formed by microinjecting or inkjet printing a fluid to form a membrane at one end of the aperture, such as in or on the outer surface opening in the housing. The fluid may be a solution comprising a resorbable material dissolved in a solvent, a suspension comprising a resorbable material in a nonsolvent, or a liquefied resorbable material.

The retention frame may be created by forming an elastic wire from, for example, a superelastic alloy or shape-memory material and "programming" the elastic wire to naturally assume a retention shape, such as by heat treatment. The retention frame then may be inserted into the retention frame housing. The likelihood of the retention frame puncturing the housing may be reduced, such as by straightening, blunting, or increasing the cross-section of the ends of retention frame, by slightly compressing the retention housing between two surfaces to elongate the opening during frame insertion, or combinations thereof. The tendency of the retention housing to stretch, twist or rotate about the retention frame may be reduced by filling the retention housing with a filling material, such as silicone adhesive, after the retention frame is loaded. In embodiments in which the retention frame comprises a low modulus elastomer, the frame may be formed with one or more windings, coils, loops or spirals so that the frame functions as a spring. For example, the retention frame may be formed by extrusion, liquid injection molding, transfer molding, or insert molding, among others. Other manufacturing methods apparent to a person of skill based on the present disclosure can be employed.

III. Use and Applications of Implantable Drug Delivery Devices

The implantable drug delivery devices described herein can be used in a variety of medical applications, particularly therapeutic and prophylactic treatments for patients.

In a particular embodiment, the devices provide pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, naproxen.

In embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote stone dissolution.

In some embodiments, the drug delivery device is used in association with the placement of a ureteral stent, such as to treat pain, urinary urgency or urinary frequency resulting from ureteral stent placement. Non-limiting examples of specific drugs for such treatment include anti-muscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In other embodiments, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include *Bacillus* Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. The drug treatment may be coupled with a conventional radiation or surgical therapy targeted to the cancerous tissue.

In still other embodiments, the device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the device is used to treat fibrosis of a genitourinary site, such as the bladder or uterus. Representative examples of drugs for the treatment of fibroids include pentoxphylline (xanthine analogue), anti-TNF, antiTGF agents, GnRH analogues, exogenous progestins, antiprogestins, selective estrogen receptor modulators, danazol, and NSAIDs.

The implantable drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

Drugs for the treatment of neurogenic bladder may be categorized into one of two general types: those for treating spastic neurogenic bladder and those for treating flaccid neurogenic bladder. In embodiments, the drug is selected from those known for the treatment of incontinence due to neurologic detrusor overactivity and/or low compliant detrusor. Examples include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In other embodiments, the drug is selected from those known for the treatment of incontinence due to neurologic sphincter deficiency. Examples include alpha adrenergic agonists, estrogens, beta-adrenergic agonists, tricyclic antidepressants (imipramine, amitriptyline). In still other embodiments, the drug is selected from those known for facilitating bladder emptying (e.g., alpha adrenergic antagonists (phentolamine) or cholinergics). In yet other embodiments, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

The device may be implanted in a body cavity or lumen. Once implanted, the device may release one or more drugs for the treatment of one or more conditions, either locally to one or more tissues at the deployment site, regionally to other tissues distal from the deployment site, or both. The release may be controlled over an extended period. Thereafter, the device may be removed, resorbed, excreted, or a combination thereof.

Figure 13:
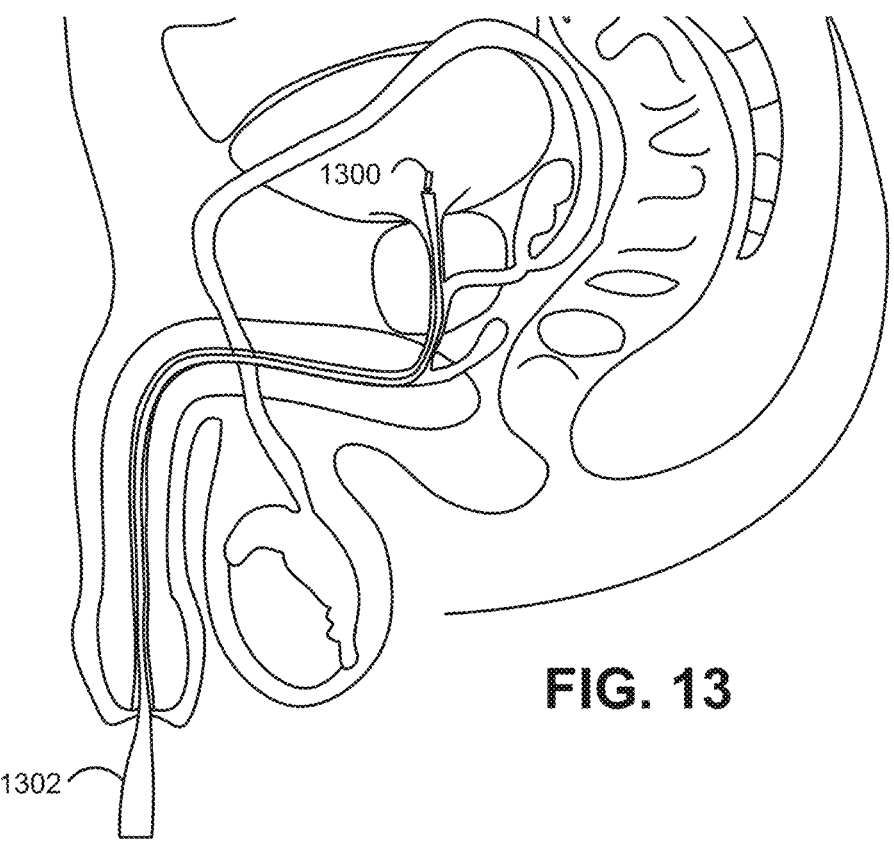
FIG. 13 is a sagittal view of a male patient, illustrating a drug delivery device exiting a deployment instrument into a bladder of the patient.
Figure 14:
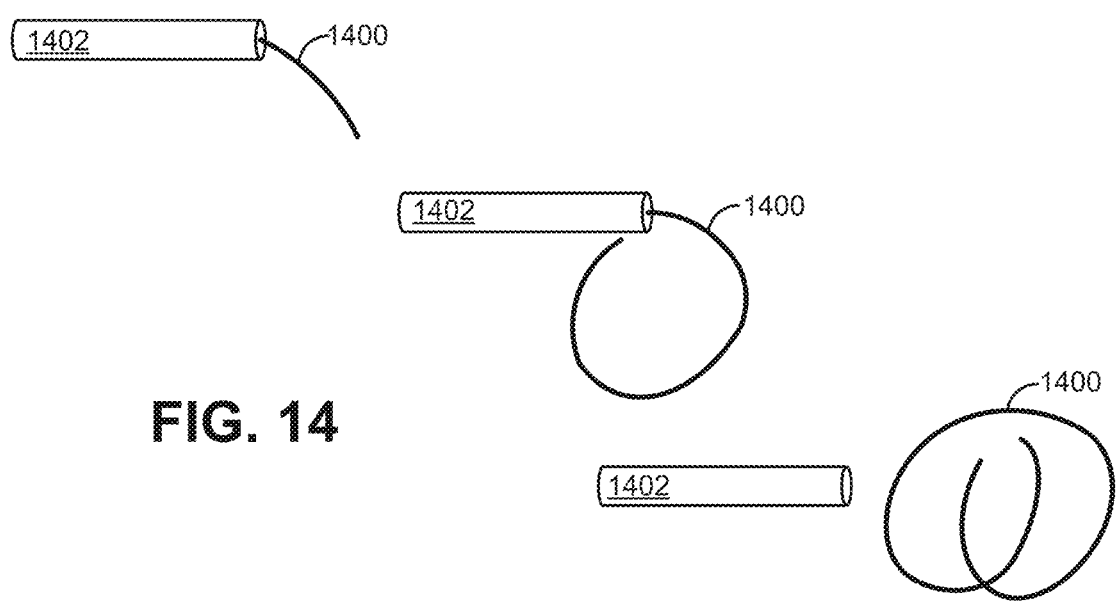
FIG. 14 schematically illustrates a drug delivery device assuming a retention shape.

In certain embodiments, the device is implanted by passing the device through a deployment instrument and releasing the device from the deployment instrument into the body. The deployment instrument may be any suitable lumen device, such as a catheter, a urethral catheter, a cystoscope, or a combination thereof, whether commercially available or specially adapted for deploying the present device. In particular embodiments, the device is implanted in the bladder, as shown in FIG. 13. The adult male anatomy is shown by way of example, although the device may be implanted into female human or child patient in other cases. A deployment instrument 1302 is inserted through the urethra to the bladder, and the device 1300 is passed through the deployment instrument 1302, driven by a stylet or flow of lubricant or other fluid, for example, until the device 1300 exits into the bladder. The device is then retained in the bladder due to the retention feature, such as by assuming a retention shape or anchoring in the bladder. An example of a device assuming a retention shape is shown in FIG. 14, which shows a device 1400 assuming a retention shape as the device exits a deployment instrument 1402.

The device may be deployed in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

Following in vivo deployment, the device releases the drug. Release may occur due to an osmotic pressure gradient between the interior and exterior of the device, the drug passing through one or more orifices or passing pores in the device under the force of osmotic pressure. Release may also occur by diffusion, whereby the drug passes through one or more orifices or passing pores in the device and/or through a drug-permeable wall of the device, due to a drug concentration gradient between the interior and exterior of the device. Combinations of these release modes within a single device are possible, and in some embodiments are preferred in order to achieve an overall drug release profile not readily achievable from either mode individually.

The selection of the form of the drug may impact release kinetics. For example, liquid drugs, including drugs in emulsion, suspension, and solution form, may be available for immediate release upon implantation, while drugs in solid form generally need to be solubilized in vivo before release. In particular, bodily fluid from the implantation site may enter the device, such as through a water-permeable wall or a passageway in the wall of the device, to dissolve the drug. For example, the drug may be solubilized upon contact with urine in cases in which the device is implanted in the bladder.

In particular embodiments, release of at least two drug payloads may occur in accordance with different release profiles, including profiles that exhibit different initial onsets of release, such as immediate and delayed release; profiles that exhibit different durations of release, such as quick and extended release; and profiles that exhibit different release rates, whether a zero-order release rate or otherwise. The overall release profile from the device may be the summation of the individualized release profiles associated with the disparate drug payloads. Continuous and extended release is thus facilitated in accordance with a desired profile. For example, the device may release a first payload relatively quickly, such as a liquid payload or a payload in a housing that operates as a fast-acting osmotic pump, and the device may release a second payload more continuously, such as from a housing that operates as a slower osmotic pump.

Release of the drug also may be delayed or modulated based on the device configuration. For example, initial onset of drug release may be delayed until a degradable timing structure, such as a timing membrane covering an aperture of the device, a timing plug blocking an aperture of the device, or a timing coating about at least a portion of the exterior of the device, degrades so that water ingress and/or drug egress through the protected aperture or wall is permitted.

The device may provide extended, continuous, intermittent, or periodic release of a desired quantity of drug over a desired, predetermined period. In various embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more. In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof.

In some embodiments, the drug delivery device is deployed into the bladder of a patient for regional drug delivery to one or more nearby genitourinary sites. The device may release drug locally to the bladder and regionally to other sites near the bladder. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions. Such delivery may provide an alternative to systemic administration, which may entail undesirable side effects or result in insufficient bioavailability of the drug.

In a particular embodiment, the drug delivery device is implanted into a bladder to locally deliver a local anesthetic agent for management of pain arising from any source, such as a disease or disorder in genitourinary tissues, or pain stemming from any bladder procedure, such as surgery, catheterization, ablation, medical device implantation, or stone or foreign object removal, among others. For example, a local anesthetic agent can be released into the bladder for regional delivery to nearby sites to manage nearby pain arising from any source, such as post-operative pain associated with the passage of a medical device into or through a ureter or other post-operative pain in sites apart from the bladder.

In particular embodiments, a device having a payload of lidocaine may be delivered to the bladder, and lidocaine may be continuously released from the device over an extended period. Local delivery of lidocaine to the urothelium of the bladder can be provided in a manner that achieves a sustained level of lidocaine above the concentration that could be obtained for an extended period via instillation, yet without the high initial peak observed with instillation and without significant systemic concentrations. Thereby, a small payload may be implanted, reducing the risk of systemic effects in the event of device failure. Implanting lidocaine in solid form permits further reducing the size of the device to reduce bladder irritation and patient discomfort. The lidocaine may be delivered without regard to the pH of the urine.

Lidocaine can be continuously released into the bladder during an initial, acute phase and during a maintenance phase. For example, the device may release at least two payloads of lidocaine in accordance with different release profiles. One of the payloads may include lidocaine hydrochloride monohydrate that is released through an orifice under the force of an osmotic pressure gradient, while another of the payloads may include lidocaine base that is released through a wall of the device via diffusion. The lidocaine base may experience a shorter delay before initial release, as the drug may be available to diffuse across the housing immediately after becoming solubilized. The lidocaine hydrochloride monohydrate may experience a longer delay before initial release, such as until enough drug has become solubilized to generate an osmotic pressure gradient. The present invention may be further understood with reference to the following non-limiting examples.

Example 1: Diffusion of Various Forms of Lidocaine Through Silicone Tubes

Figure 15:
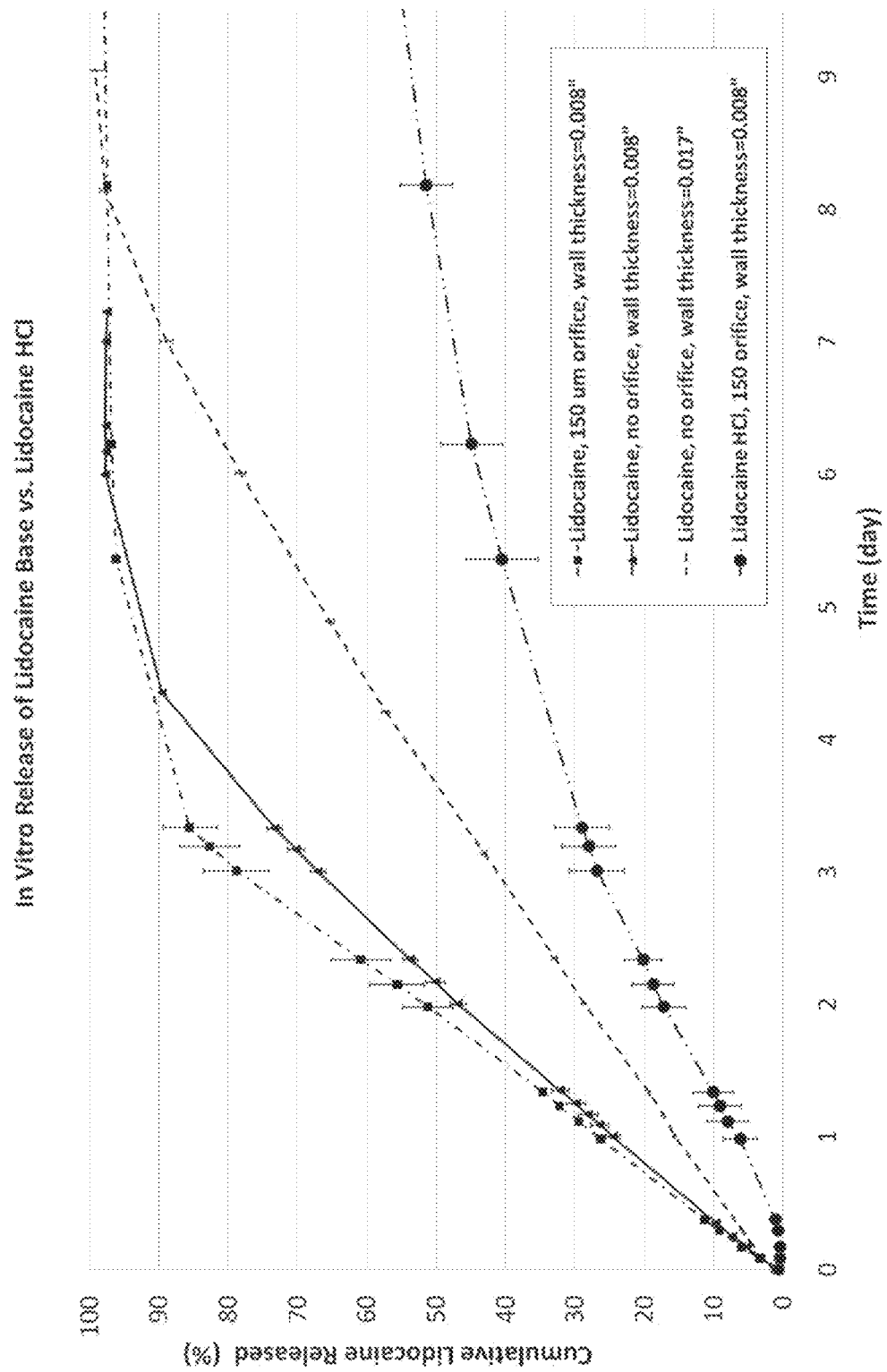
FIG. 15 is a graph illustrating the release as a function of time of either lidocaine hydrochloride monohydrate or lidocaine base from tubes of various construction.

A study was performed to determine the feasibility of delivering lidocaine via diffusion through a silicone wall of a tubular drug housing. Devices were formed form silicone tubes, each having a length of about 3 cm. The devices were loaded with solid drug tablets of either lidocaine hydrochloride monohydrate or lidocaine base, for a total payload of about 60 mg. The devices were tested in vitro in water at about 37° C. Release profile data, shown in FIG. 15, demonstrates that it is feasible to deliver lidocaine base via diffusion through a silicone wall without an aperture.

Figure 16:
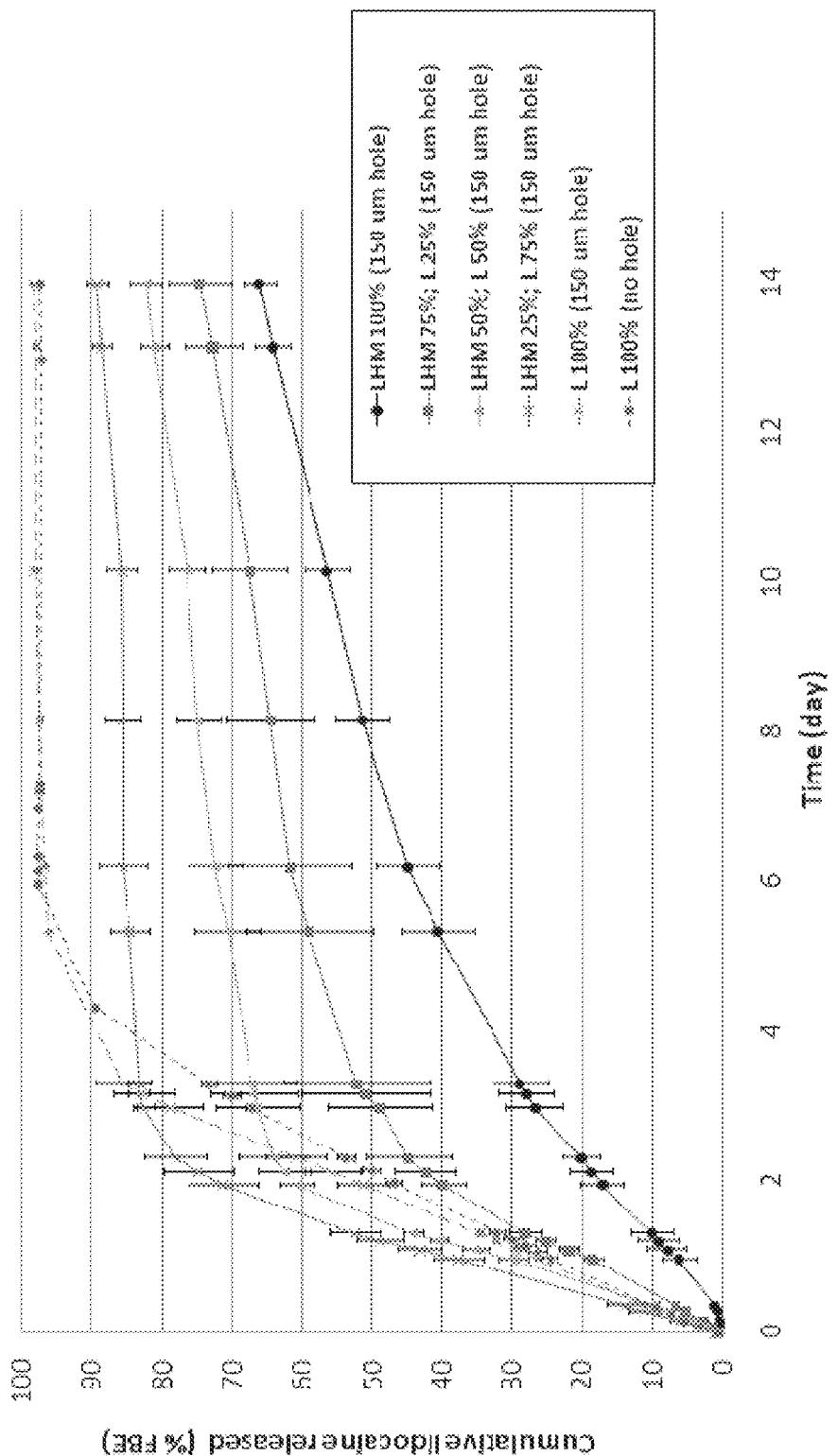
FIG. 16 is a graph illustrating the release as a function of time of lidocaine hydrochloride monohydrate, lidocaine base or a combination thereof from tubes of various construction.

A study was performed to determine the feasibility of delivering lidocaine via diffusion through a silicone wall of a tubular drug housing. Devices were formed form silicone tubes, each having an inner diameter of about 0.060 inches, an outer diameter of 0.076 inches, and a length of about 3 cm. The devices were loaded with solid drug tablets of lidocaine, for a total payload of about 60 mg. Some of the devices included an aperture formed through the tube wall, the aperture having a diameter of 150 µm. These devices were loaded with solid tablets of either lidocaine hydrochloride monohydrate (LHM) or a combination of lidocaine hydrochloride monohydrate and lidocaine base (L). Other devices did not include an aperture and were loaded with solid drug tablets of lidocaine base. The devices were tested in vitro in water at about 37° C. Release profile data, shown in FIG. 16, demonstrates that it is feasible to deliver lidocaine base via diffusion through a silicone wall without an aperture.

Figure 17:
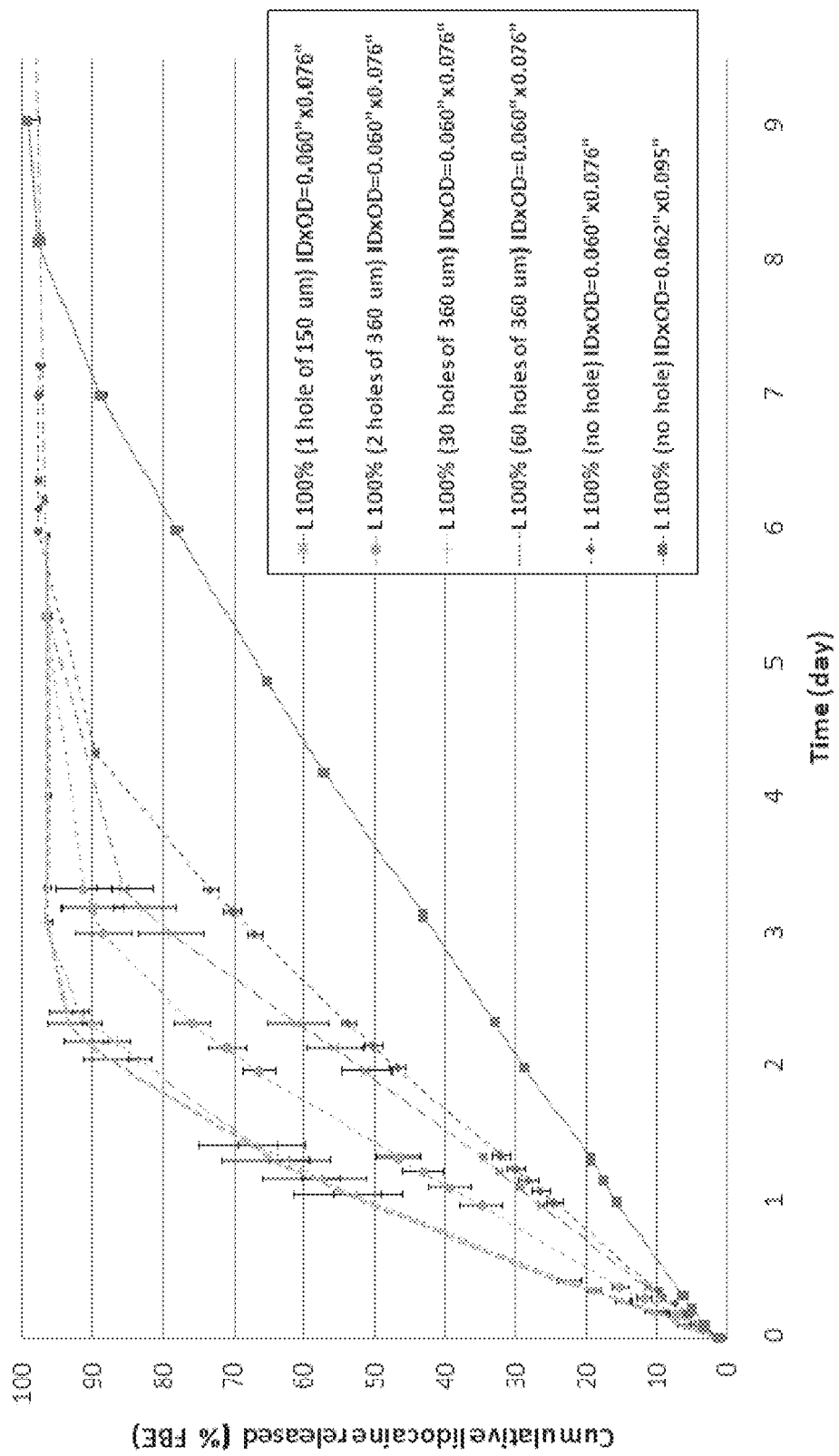
FIG. 17 is a graph illustrating the release of lidocaine base as a function of time from tubes of various construction.

Another study was performed to investigate the feasibility of delivering lidocaine base via diffusion through a silicone wall and from an aperture in a silicone wall. Devices were formed form silicone tubes having a length of about 3 cm. The devices were loaded with solid drug tablets of lidocaine base, for a total payload of about 60 mg. Five devices had an inner diameter of about 0.060 inches and an outer diameter of 0.076 inches. The first device had one aperture with a diameter of about 150 µm, the second device had two apertures that each had a diameter of about 360 µm, the third device had thirty apertures that each had a diameter of about 360 µm, the fourth device had sixty apertures that each had a diameter of about 360 µm, and the fifth device had no apertures. A sixth device had an inner diameter of about 0.062 inches, an outer diameter of 0.095 inches, and no apertures. The devices were tested in vitro in water at about 37° C. Release profile data, shown in FIG. 17, demonstrates that lidocaine base can be released from a silicone tube without any apertures and that the release rate can be increased by adding apertures to the device.

Example 2: Example Release Rates for Silicone-Based Devices Loaded with Lidocaine Base Theoretical release rates were calculated for two drug portions formed from tubular silicone walls having no apertures, the theoretical release occurring primarily via diffusion across the silicone wall. The steady state release rate (R) is a function of the permeability (D) of the wall, the inner diameter (ID) of the wall, the outer diameter (OD) of the wall, the length (L) of the wall, and the solubility (S) of the drug, wherein R=(2 DSL)/ln(OD/ID). A tubular silicone drug portion having a payload of 60 mg of lidocaine base, a length of 3 cm, an inner diameter of 1.52 mm, and an outer diameter of 1.93 mm was calculated to exhibit a release rate of 13 mg/day. Another tubular silicone drug portion having a payload of 800 mg of lidocaine base, a length of 14 cm, an inner diameter of 2.58 mm, and an outer diameter of 3.31 mm was calculated to exhibit a release rate of 57 mg/day.

While particular embodiments of an implantable drug delivery device have been disclosed in detail in the foregoing description and figures for purposes of example, those skilled in the art will understand that variations and modifications may be made without departing from the scope of the disclosure. For instance, features' illustrated or described as part of one embodiment can be used on another embodiment to yield a still further embodiment. All such variations and modifications are intended to be included within the scope of the present disclosure, as protected by the following claims and the equivalents thereof.

We claim:

1. An intravesical drug delivery device for controlled drug delivery comprising:
a drug reservoir component which comprises an elastic tube having at least one lumen bounded by a porous sidewall having an open-cell structure, a closed-cell structure, or a combination thereof;
a retention frame coupled to the drug reservoir component; and
a first drug formulation contained within the at least one lumen, wherein the first drug formulation is in the form of a plurality of aligned tablets, wherein the tablets are cylindrical with flat end faces,
wherein the device reservoir component is deformable between a low-profile deployment shape and a coiled retention shape, and
wherein the retention frame comprises one or more loops or curls when the device reservoir component is in the coiled retention shape and biases the device reservoir component to return from the low-profile deployment shape to the coiled retention shape.

2. The device of claim 1, wherein the first drug formulation is configured to become solubilized in vivo for release through the porous sidewall.

3. The device of claim 1, further comprising a second drug formulation.

4. The device of claim 3, wherein the first drug formulation comprises a high solubility drug and the second drug formulation comprises a low solubility drug.

5. The device of claim 1, wherein the porous sidewall has an open-cell structure.

6. The device of claim 5, wherein the porous sidewall comprises at least one passageway, wherein the passageway is an aperture formed completely through the porous sidewall by drilling, punching, or molding.

7. The device of claim 5, wherein the porous sidewall is coated to form a closed-cell structure.

8. The device of claim 5, wherein the porous sidewall comprises pores randomly distributed throughout the porous sidewall.

9. The device of claim 1, further comprising a retention frame lumen in which the retention frame is disposed.

10. An intravesical drug delivery device for controlled drug delivery comprising:
a device body comprising a drug reservoir component which comprises an elastic tube having a drug reservoir lumen bounded by a porous sidewall having an open-cell structure;
a retention frame coupled to the drug reservoir component; and
a first drug formulation contained within the drug reservoir lumen, wherein the first drug formulation is in the form of a plurality of aligned tablets, wherein the tablets are cylindrical with flat end faces,
wherein the device body is deformable between a low-profile deployment shape and a coiled retention shape, and
wherein the retention frame comprises one or more loops or curls when the device body is in the coiled retention shape and biases the device body to return from the low-profile deployment shape to the coiled retention shape.

11. The device of claim 10, wherein the device body further comprises a retention frame lumen in which the retention frame is disposed, wherein the drug reservoir lumen and the retention frame lumen are parallel to one another over the full length of the device body, in both the deployment shape and the coiled retention shape.

12. An intravesical drug delivery device for controlled drug delivery comprising:
a device body comprising a drug reservoir component which comprises an elastic tube having a drug reservoir lumen bounded by a porous sidewall having an open-cell structure;
a retention frame coupled to the drug reservoir component; and
a drug formulation contained within the drug reservoir lumen, wherein the drug formulation is in the form of a plurality of aligned tablets, wherein the tablets are cylindrical with flat end faces,
wherein:
the intravesical drug delivery device is deformable between a low-profile deployment shape and a coiled retention shape, and
the retention frame comprises one or more windings, coils, loops or spirals so that the retention frame functions as a spring to bias the intravesical drug delivery device to return from the low-profile deployment shape to the coiled retention shape.

13. The device of claim 12, wherein the device body further comprising a retention frame lumen in which the retention frame is disposed, wherein the drug reservoir lumen and the retention frame lumen are parallel to one another over the full length of the device body, in both the deployment shape and the coiled retention shape.

* * * * *

UNITED STATES PATENT AND TRADEMARK OFFICE
CERTIFICATE OF CORRECTION

| | | |
|---|---|---|
| PATENT NO. | : 11,135,161 B2 | Page 1 of 1 |
| APPLICATION NO. | : 15/815843 | |
| DATED | : October 5, 2021 | |
| INVENTOR(S) | : Heejin Lee et al. | |

It is certified that error appears in the above-identified patent and that said Letters Patent is hereby corrected as shown below:

On the Title Page

Item (73) should read:
--TARIS BIOMEDICAL LLC, Lexington, MA (US)--

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*